United States Patent
Dos Santos Baltazar De Lima et al.

(10) Patent No.: US 12,336,977 B2
(45) Date of Patent: Jun. 24, 2025

(54) NITENIN ANALOGUE COMPOUNDS AND THEIR USE IN THE TREATMENT OF CHRONIC AND ACUTE PAIN

(71) Applicant: SEA4US-BIOTECNOLOGIA E RECURSOS MARINHOS, LDA., Sagres (PT)

(72) Inventors: Pedro Afonso Dos Santos Baltazar De Lima, Cascais (PT); Beatriz Szwarc Dos Santos, Lisbon (PT); Ana Rosa Maço Abreu, Pombal (PT); André Emanuel Pinheiro Bastos, Lisbon (PT); Rui Gomes, São Domingos de Rana (PT); Marisa Isabel Lopes De Sousa, Benavente (PT); Joana Maria Monteiro Serrão, Charneca da Caparica (PT); Sílvia Patrícia Pena Lino, Lisbon (PT); Patrícia Isabel Da Silveira Máximo, Lisbon (PT); Luísa Maria Pinto Ferreira, Mem Martins (PT); Paula Cristina De Sério Branco, Igreja Nova MFR (PT); Henrique Sovela Mourão, Costa de Caparica (PT); Vanessa Alexandra Rosado Sabino, São Salvador da Aramenha (PT); Ming Him Tong, Aberdeen (GB); Laurent Alain Claudetrembleau, Danestone Aberdeen (GB); Ana Maria Ferreira Da Costa Lourenço, Lisbon (PT); Miguel Angelo Segão Mondragão, Linda-a-Velha (PT)

(73) Assignee: SEA4US—BIOTECNOLOGIA E RECURSOS MARINHOS, LDA., Sagres (PT)

( * ) Notice: Subject to any disclaimer, the term of this patent is extended or adjusted under 35 U.S.C. 154(b) by 0 days.

(21) Appl. No.: 17/631,135
(22) PCT Filed: Jul. 22, 2020
(86) PCT No.: PCT/IB2020/056915
§ 371 (c)(1),
(2) Date: Jan. 28, 2022
(87) PCT Pub. No.: WO2021/019373
PCT Pub. Date: Feb. 4, 2021

(65) Prior Publication Data
US 2022/0288017 A1   Sep. 15, 2022

(30) Foreign Application Priority Data
Jul. 31, 2019   (PT) ........................................ 115685

(51) Int. Cl.
*A61K 31/365*   (2006.01)
*A61K 31/353*   (2006.01)
(Continued)

(52) U.S. Cl.
CPC .......... *A61K 31/365* (2013.01); *A61K 31/353* (2013.01); *A61P 25/04* (2018.01); *C07D 307/28* (2013.01); *C07D 307/36* (2013.01)

(58) Field of Classification Search
CPC ..... A61K 31/365; A61K 31/353; A61P 25/04; A61P 3/10; A61P 25/02; A61P 37/00;
(Continued)

(56) References Cited

U.S. PATENT DOCUMENTS

2014/0234343 A1   8/2014   Lee et al.
2015/0284405 A1   10/2015   Trzupek et al.

FOREIGN PATENT DOCUMENTS

CN   106146530 A   11/2016
WO   02072542 A2   9/2002
(Continued)

OTHER PUBLICATIONS

Langlais et al., Scope and Limitations of Xanthate-Mediated Synthesis of Functional γ-Thiolactones, ACS Omega, 3(12), 17732-17742 (Year: 2018).*
(Continued)

*Primary Examiner* — Taylor V Oh
(74) *Attorney, Agent, or Firm* — Arrigo, Lee, Guttman & Mouta-Bellum, LLP; Carla Mouta-Bellum

(57) ABSTRACT

The present disclosure relates to nitenin analogue compounds (of formulas I, II, III and IV) and their use as pharmaceutical agent in the treatment, prevention or reduction of both acute and chronic pain. The mode of action disclosed herein allows nitenin and nitenin analogue compounds to act as analgesic through reduction of $K^{30}$ currents rather than their potentiation. Related to their high efficacy
(Continued)

in the treatment of pain, these compounds are highly selective for slow voltage-activated potassium ($K^{30}$) currents expressed in the small diameter dorsal root neurons (sDRGns), mainly on those mediated by the voltage-dependent potassium channel ($K_V$), $K_V1.3$. Such findings, together with those showing that nitenin and nitenin analogue compounds act as activity dependent blockers also lead to very reduced side-effects. The results disclosed herein show that nitenin and nitenin analogue compounds described herein are a viable alternative to the already existing pharmaceutical compounds used in the treatment of pain.

15 Claims, 12 Drawing Sheets

(51) Int. Cl.
  *A61P 25/04* (2006.01)
  *C07D 307/28* (2006.01)
  *C07D 307/36* (2006.01)
(58) Field of Classification Search
  CPC .. A61P 5/50; A61P 25/08; A61P 37/06; C07D 307/28; C07D 307/36; C07D 407/14; C07D 407/06
  USPC .......................................................... 514/456
  See application file for complete search history.

(56) References Cited

FOREIGN PATENT DOCUMENTS

| WO | 2007009462 A2 | 1/2007 |
| WO | 2010040803 A2 | 4/2010 |
| WO | 2015153184 A1 | 10/2015 |
| WO | 2021019373 A1 | 2/2021 |

OTHER PUBLICATIONS

International Application No. PCT/IB2020/056915: PCT International Search Report, dated Dec. 12, 2020, 7 pages.
International Application No. PCT/IB2020/056915: PCT Written Opinion, dated Dec. 12, 2020, 11 pages.
Gouault et al., "Solid-phase Synthesis, Antiviral Activity and Cytotoxicity of Some Functionalized Lactones", Pharmacy and Pharmacology Communications, vol. 5, No. 3, Mar. 1, 1999, 159-163.
Johansson et al., "Biologically Active Secondary Metabolites from the Ascomycete A111-95 2. Structure Elucidation.", The Journal of Antibiotics, vol. 55, No. 1, Jan. 1, 2002, 104-106.
Braun et al., "Synthesis and Determination of the Absolute Configuration of Fugomycin and Desoxyfugomycin: CD Spectroscopy and Fungicidal Activity of Butenolides", Chemistry—A European Journal, vol. 10, No. 18, Sep. 20, 2004, 4584-4593.
Fattorusso et al., "Isolation and structure of nitenin and dihydronitenin, new furanoterpenes from Spongia nitens", Tetrahedron, vol. 27, No. 16, Jan. 1, 1971, 3909-3917.
Heemann et al., "Cytotoxic and Apoptotic Activity of Majoranolide from Mezilaurus crassiramea on HL-60 Leukemia Cells", Evidence-Based Complementary and Alternative Medicine, vol. 2019, Mar. 3, 2019, 1-8.
Alves et al., "Alkene lactones from *Persea fulva* (Lauraceae): Evaluation of their effects on tumor cell growth in vitro and molecular docking studies", Bioorganic Chemistry, vol. 86, May 31, 2019, 665-673.
Mendgen et al., "Structure-activity relationships of tulipalines, tuliposides, and related compounds as inhibitors of MurA", Oct. 1, 2010, vol. 20, No. 19, 5757-5762.
Song et al., "Homochiral 4-hydroxy-5-hexenoic acids and their derivatives and homologues from carbohydrates", Tetrahedron Asymmetry, Pergamon Press Ltd, Oxford, GB, vol. 12, No. 3, Mar. 5, 2001, 387-391.
Yamamoto et al., "Identification of putative metabolites of docosahexaenoic acid as potent PPAR@c agonists and antidiabetic agents", Feb. 1, 2005, vol. 15, No. 3, 517-522.
PCT International Search Report dated Nov. 4, 2020, in connection with International Application No. PCT/IB2020/056918, related but not foreign counterpart application, all pages.
PCT Written Opinion, dated Nov. 4, 2020, in connection with International Application No. PCT/IB2020/056918, related but not foreign counterpart application, all pages.
English translation of CNCN106146530A.
EP Examination Report issued Mar. 28, 2024 in foreign counterpart EP Application Serial No. n° 20761628.5 (6 pages).
Fontana, Angelo, et al. "Chemical studies of Cadlina molluscs from the Cantabrian Sea (Atlantic Ocean)" Comp. Biochem. Physiol. vol. 111B, No. 2, pp. 283-290, 1995.
Fontana, Angelo, et al. "Structural and Stereochemical Studies of C-21 Terpenoids from Mediterranean Spongiidae Sponges" J. Nat. Prod. 1996, 59, 869-872.
Lenis, Luis et al. "Isonitenin and Acetylhomoagmatine New Metabolites From the Sponges Spongia Officinalis and Cliona Celata Collected At the Galician Coast (NW Spain)" Natural Product Letters vol. 8. pp. 15-23.
Noyer, Charlotte et al. "Patterns of Chemical Diversity in the Mediterranean Sponge Spongia lamella" PLoS ONE, Jun. 2011 | vol. 6 | Issue 6 | e20844, pp. 1-11.
Rueda, Ana et al. "New Metabolites from the Sponge Spongia agaricina" J. Nat. Prod. 1998, 61, 258-261.
Dyson G., May P. "Chemistry of synthetic drugs", translated from English. Moscow, Mir, 1964, p. 12-19).
Belikov V.G., Pharmaceutical Chemistry, a course book, 2007, Moscow, Medpress-inform publisher, pp. 27-29.
Mashkovskiy M.D., Drugs, Moscow, Medicine publisher, 1993, Part 1, p. 8.
K.Kümmererer, Pharmaceuticals in the environment, Annual Review of Environment and Resources, 2010, V.35, p. 57-75, doi: 10.1146/annurev-environ-052809-161223.
CAS1629451_87_1.
EP Examination Report issued Mar. 28, 2024 in foreign counterpart EP Application No. n° 20761628.5 (6 pages).
Fontanan, Angelo, et al. "Chemical studies of Cadlina molluscs from the Cantabrian Sea (Atlantic Ocean)" Comp. Biochem. Physiol. vol. 111B, No. 2, pp. 283-290, 1995.
K.Kümmererer, Pharmaceuticals in the environment, Annual Review of Environment and resources, 2010, v. 35, p. 57-75, doi: 10.1146/aanurev-environ-052809-161223.
Spela, Gubic et al., "Immunsuppresive effects of thiophene-based KV1.3 inhibtors" European Journal of Medicinal Chemistry, vol. 259 Nov. 1, 2023 p. 115561 (17 pages).

\* cited by examiner

V

VI

VII

VIII

A

B

NITENIN ANALOGUE COMPOUNDS AND THEIR USE IN THE TREATMENT OF CHRONIC AND ACUTE PAIN

CROSS-REFERENCE TO RELATED APPLICATIONS

This application is a U.S. National Stage Entry of PCT/IB2020/056915, filed Jul. 22, 2020, and claims priority to Portuguese Patent Application No. 115685, filed Jul. 31, 2019, both of which are herein incorporated by reference in their entirety.

TECHNICAL FIELD

The present disclosure relates to nitenin analogue compounds and their use as analgesic agents for the treatment, prevention or reduction of chronic pain and acute pain.

BACKGROUND ART

Acute pain usually arises on suddenly and the cause is specific. It is sharp in quality. Acute pain commonly does not last longer than three-six months. It goes away when there is no longer an underlying cause for the pain. A person can then go on with life as usual. Exemplary causes of acute pain include surgery, broken bones, dental work, burns and cuts, labor and childbirth.

Chronic pain is defined as pain persisting for more than three months or beyond the natural recovery time. Pain signals keep firing in the nervous system, even without physiological stimuli, for weeks, months or years. It arises in many medical conditions, including for example diabetes, arthritis, migraine, fibromyalgia, cancer, back pain, shingles, sciatica, trigeminal neuralgia and previous trauma or injury. Chronic pain can cause disability significantly interfering with a person's quality of life and causing a huge negative impact on society. It affects 21% of the world's population (1.5 billion people) and has enormous economic costs associated. In the United States of America (USA) alone, in 2010, it was estimated that there were $560-635 billion spent in salary losses and low productivity, and health care costs. With increasing aged population, the demand for adequate and better pain management therapies is on the rise.

Although there are effective and safe analgesics for mild pain, treatments for moderate and severe chronic pain are, in most cases, ineffective and cause limiting and noxious side effects. Therefore, the major problem for patients of most types of chronic pain is the inexistence of a truly adequate pharmaceutical treatment, at least without inflicting important limiting side-effects. For example, against situations of moderate to severe pain levels, opioid derivatives do alleviate pain but co-inflict important noxious effects like habituation, addiction and loss of drive or motivation. The use of opioids became an epidemical problem in several countries, with increasing addiction situations and a heavy burden for the society. For example, in USA, the number of deaths related to opioids use is much greater than the number of deaths caused by illicit drugs. Other kinds of drugs are used for treatments, including antidepressants, antiepileptic drugs, and non-steroidal anti-inflammatory drugs (NSAIDs), but these are either not efficient or also cause relevant side-effects.

Other, such as more recent treatments for moderate to severe pain, closer to the pharmacological context of the present invention, include ion channel modulators. Ion channels are key proteins present in neuronal membranes that shape electrical signaling, and thus, pain signals in nerves. Neurons involved in pain sensing (nociception) located in the peripheral nervous system include those that have their cell bodies located in the nervous ganglia (dorsal root ganglia-DRG) outside the spinal cord (or trigeminal ganglia-TG, in the head). Such nociceptive fibers are the first peripheral nerve sensors involved in the physiological pathway that leads to the brain perception of pain.

In terms of currently available therapies involving ion channels modulation for the treatment of pain, there are only two cases already in the market.

Notwithstanding, they are only partially effective or still cause relevant side effects, due to the type of ion channel being modulated. Such medications are:

Topic capsaicin, a Transient Receptor Potential Cation channel subfamily V member 1 (TRPV1) channel agonist;

Intrathecal injection of ziconotide (Prialt®), an N-type voltage-gated calcium channel blocker, obtained from a marine cone snail; in this case, acting not peripherally, but centrally.

New products currently under clinical development (in the pipeline of several biotechnology and pharmaceutical companies but which haven't been approved for commercialization) include new opioids with certain modifications (making them less addictive) and other ion channel modulators tackling ion channels known to be involved in pain, but more adequate than TRPV1 and N-type voltage-gated calcium channels (e.g. ion channels such as other TRPs, voltage-gated sodium channels $Na_v1.7$ and $Na_v1.8$).

As far as it is currently known from the prior art, there are only two agents acting on a $K^+$ channel that are currently under non-clinical or clinical trials for pain treatment.

a) The anticonvulsant retigabine (Phase II) attenuates nociceptive behaviors in rat models of persistent and neuropathic pain. Retigabine works primarily as a $K^+$ channel opener—that is, by activating a certain family of voltage-gated potassium (Kv7/M) channels in the brain.

b) Other channel modulator BL-7050 (pre-clinical phase), based on the molecular structure of diclofenac (a NSAID) binds to and stabilizes the body's potassium channels, controlling their hyper-excitability (by keeping it open) and preventing the occurrence of pain by keeping the channels open for the outflow of $K^+$.

However, despite substantial pharmaceutical research, such ion channels still seek better and specific blockers/potentiators clinically approved, leaving patients with no alternative besides pharmaceutical drugs with heavy side-effects.

SUMMARY

In one aspect, the present disclosure relates to nitenin analogue compounds and their use as analgesics for the treatment, prevention or reduction of chronic pain and acute pain.

Without wanting to be bound by theory, in some aspects, the present invention differentiates from the presently existing solutions not only by its chemical nature but also by its mode of action. By "switching off" or by reducing the activity of the nociceptive fibers with bioactive molecules, brain perception of pain is predicted to be blocked or attenuated, but in a manner that may not affect brain functioning, because these molecules may act in the "peripheral portion of pain signaling pathway", prior to the central nervous system.

Any aspect or embodiment described herein may be combined with any other aspect or embodiment as disclosed herein. While the present invention has been described in conjunction with the detailed description thereof, the foregoing description is intended to illustrate and not limit the scope of the present invention, which is defined by the scope of the appended claims. Other aspects, advantages, and modifications are within the scope of the following embodiments/claims.

Embodiment 1. Compounds of formula I, II, III and IV, pharmaceutically acceptable salts or prodrug thereof,

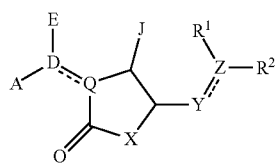

(I)

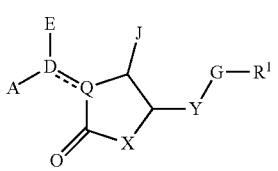

(II)

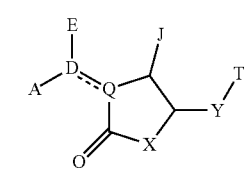

(III)

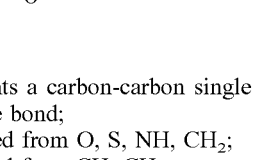

(IV)

wherein

═ represents a carbon-carbon single bond or a carbon-carbon double bond;

X is selected from O, S, NH, $CH_2$;
Y is selected from CH, $CH_2$;
Z is selected from C, N;
G is selected from O, S;
T is selected from OH, SH, $NH_2$, halogen;
$R^1$ and $R^2$ are independently selected from H, alkyl, alkenyl, cycloalkyl, aryl or —$CH_2$—$R^3$; wherein $R^3$ is selected from aryl, cycloalkyl, heteroaryl, —$R^4$-$R^5$; wherein $R^4$ is selected from alkyl, alkenyl; wherein $R^5$ is selected from aryl, substituted or unsubstituted heteroaryl, substituted or unsubstituted gama-lactone;
Q is selected from C, CH;
D is selected from C, CH, $CH_2$;
One of A and E is H and the other is selected from H, OH, SH, aryl, alkyl, alkenyl, $R^6$-$R^7$, wherein $R^6$ is selected from alkyl, alkenyl, and $R^7$ is selected from alkyl, alkenyl, substituted or unsubstituted aryl, substituted or unsubstituted heteroaryl, substituted or unsubstituted gama-lactone;
J is selected from H, OH, SH, $NH_2$, halogen;
wherein the compound is not nitenin, dihydronitenin nor their respective isomers, enantiomers and stereoisomers.

Embodiment 2. The compounds of formula IV according to embodiment 1, wherein

X is O;
Y is CH;
Z is C;
$R^1$ is H;
$R^2$ is H; and
J is OH.

Embodiment 3. The compounds of formula IV according to embodiment 1, wherein

X is O;
Y is CH;
Z is C;
$R^1$ is alkyl;
$R^2$ is —$CH_2$—$R_3$; wherein $R^3$ is —$R^4$-$R^5$; wherein $R^4$ is alkyl and $R^5$ is heteroaryl J is OH.

Embodiment 4. The compounds of formula II according to embodiment 1, wherein

X is O;
Y is $CH_2$;
G is O;
$R^1$ is H;
J is H;
Q is C;
D is C;
E is H;
A is —$R^6$-$R^7$; wherein $R^6$ is alkyl and $R^7$ is heteroaryl.

Embodiment 5. The compounds of formula II according to embodiment 1, wherein

X is O;
Y is $CH_2$;
G is O;
$R^1$ is H;
J is H;
Q is C;
D is C;
E is —$R^6$—$R^7$; wherein $R^6$ is alkyl and $R^7$ is heteroaryl;
A is H.

Embodiment 6. The compounds of formula I, II, III and IV, according to embodiment 1, wherein $R^7$ is not furan-3-yl.

Embodiment 7. Compounds of formula I, II, III and IV, pharmaceutically acceptable salts or prodrug thereof,

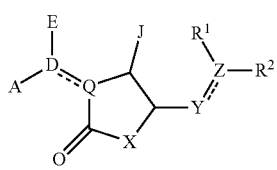

(I)

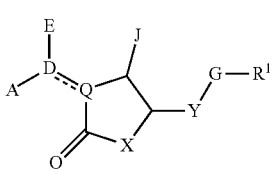

(II)

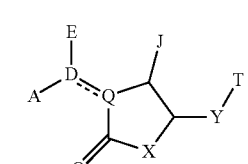

(III)

-continued

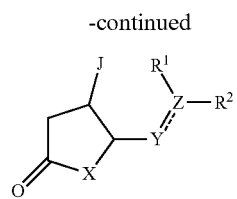
(IV)

wherein
═ represents a carbon-carbon single bond or a carbon-carbon double bond;
X is selected from O, S, NH, CH$_2$;
Y is selected from CH, CH$_2$;
Z is selected from C, N;
G is selected from O, S;
T is selected from OH, SH, NH$_2$, halogen;
R$^1$ and R$^2$ are independently selected from H, alkyl, alkenyl, cycloalkyl, aryl or —CH$_2$—R$^3$; wherein R$^3$ is selected from aryl, cycloalkyl, heteroaryl, —R$^4$-R$^5$; wherein R$^4$ is selected from alkyl, alkenyl; wherein R$^5$ is selected from aryl, substituted or unsubstituted heteroaryl, substituted or unsubstituted gama-lactone;
Q is selected from C, CH;
D is selected from C, CH, CH$_2$;
One of A and E is H and the other is selected from H, OH, SH, aryl, alkyl, alkenyl, R$^6$-R$^7$, wherein R$^6$ is selected from alkyl, alkenyl, and R$^7$ is selected from alkyl, alkenyl, substituted or unsubstituted aryl, substituted or unsubstituted heteroaryl, substituted or unsubstituted gama-lactone;
J is selected from H, OH, SH, NH$_2$, halogen;
for use as a pharmaceutical ingredient.

Embodiment 8. The compounds of formula I for use as pharmaceutical ingredient according to embodiment 7, wherein;
X is O;
Y is CH;
Z is C;
R$^1$ is alkyl;
R$^2$ is —CH$_2$—R$^3$; wherein R$^3$ is —R$^4$-R$^5$; wherein R$^4$ is alkyl and R5 is heteroaryl;
Q is C;
D is C;
A is —R$^6$-R$^7$; wherein R$^6$ is alkyl and R$^7$ is heteroaryl;
E is H; and
J is H.

Embodiment 9. The compounds of formula IV for use as pharmaceutical ingredient according to embodiment 7, wherein;
X is O;
Y is CH;
Z is C;
R$^1$ is H;
R$^2$ is H; and
J is OH.

Embodiment 10. The compounds of formula IV for use as pharmaceutical ingredient, wherein;
X is O;
Y is CH;
Z is C;
R$^1$ is alkyl;
R$^2$ is —CH2-R3;wherein R$^3$ is —R$^4$-R$^5$; wherein R$^4$ is alkyl and R$^5$ is heteroaryl J is OH.

Embodiment 11. The compounds of formula II for use as pharmaceutical ingredient according to embodiment 7, wherein;
X is O;
Y is CH$_2$;
G is O;
R$^1$ is H;
J is H;
Q is C;
D is C;
E is H;
A is —R$^6$-R$^7$; wherein R$^6$ is alkyl and R$^7$ is heteroaryl.

Embodiment 12. The compounds of formula II for use as pharmaceutical ingredient according to embodiment 7, wherein;
X is O;
Y is CH$_2$;
G is O;
R$^1$ is H;
J is H;
Q is C;
D is C;
E is —R$^6$-R$^7$; wherein R$^6$ is alkyl and R$^7$ is heteroaryl;
A is H.

Embodiment 13. For pharmaceutical use, the compounds of formula I, II, III and IV, of the present patent application is used in warm-blooded vertebrates, preferably mammals, more preferably humans, in doses ranging from 0.1 µg/ml blood (6 µg/Kg body weight) to 30 µg/ml blood (1.8 mg/Kg body weight). The previously-mentioned effective dose range is for intravenous administration and it may differ in other routes of administration.

Embodiment 14. The compounds of formula I, II, III and IV pharmaceutical salts or prodrug thereof are used in the treatment, prevention or reduction of pain in an individual in need thereof, more specifically with acute or chronic pain. Acute and chronic pain is intended to include, but is not limited to, at least one of the following: neuropathic pain, nociceptive pain, psychogenic or somatogenic pain, diabetic neuropathic pain, post-herpetic pain, low-back pain, radiculopathy pain, musculoskeletal pain, post-operative and post-traumatic pain, phantom pain, surgical pain, wound associated pain, chemotherapy-induced peripheral neuropathic pain, short-term/acute or long-term/chronic inflammatory pain, rheumatic pain, arthritic pain, pain associated with osteoarthritis, myofascial pain, migraine, orofacial chronic pain, trigeminal neuralgia, pain associated with cancer, pain associated with fibromyalgia, hyperalgesia syndromes, pain associated with infections, HIV related pain, sprains and strains, hyperalgesia, somatogenic pain, psychogenic pain, heat induced pain, physical pain, nociceptive pain, rheumatic pain, headache, pelvic pain, bladder pain, myofascial, vascular pain, migraine wound, wound associated pain, arthritic pain, somatic visceral pain, phantom pain, radiculopathy, lumbar pain, visceral pain, bowel pain, and pain associated with osteoarthritis.

Embodiment 15. The compounds of formula I, II, III and IV, pharmaceutical salts or prodrug thereof are used in the treatment of autoimmune disorders, due to effects described upon Kv1.3, a target for such disorders.

Embodiment 16. The compounds of formula I, II, III and IV, pharmaceutical salts or prodrug thereof are used in the treatment of diabetes, considering their effect on Kv1.3 channel believed to be related to insulin-sensitivity, insulin-resistance related syndromes and obesity.

Embodiment 17. The compounds of formula I, II, III and IV, pharmaceutical salts or prodrug thereof are used as antiepileptic and antiseizures agents.

Embodiment 18. The compounds of formula I, II, III and IV, for use in the treatment or prophylaxis of a disease in which Kv1.3 channels are involved.

Embodiment 19. A pharmaceutical composition comprises a pharmaceutically acceptable diluent or carrier and a combination of active ingredients, wherein said active ingredients comprise at least one compound according to formula I, II, III and IV or a pharmacologically acceptable salt or prodrug thereof.

Embodiment 20. A method of treating pain in a subject in need thereof, comprising administering to the subject having pain a therapeutically effective amount of a compound of formula I, II, III and IV.

Embodiment 21. The method according to embodiment 19, wherein the pain is of an acute and chronic pain types selected from neuropathic pain, nociceptive pain, psychogenic or somatogenic pain, diabetic neuropathic pain, post-herpetic pain, low-back pain, radiculopathy pain, musculoskeletal pain, post-operative and post-traumatic pain, phantom pain, surgical pain, wound associated pain, chemotherapy-induced peripheral neuropathic pain, short-term/acute or long-term/chronic inflammatory pain, rheumatic pain, arthritic pain, pain associated with osteoarthritis, myofascial pain, migraine, orofacial chronic pain, trigeminal neuralgia, pain associated with cancer, pain associated with fibromyalgia, hyperalgesia syndromes, pain associated with infections, HIV related pain, sprains and strains, hyperalgesia, somatogenic pain, psychogenic pain, heat induced pain, physical pain, nociceptive pain, rheumatic pain, headache, pelvic pain, bladder pain, myofascial, vascular pain, migraine wound, wound associated pain, arthritic pain, somatic visceral pain, phantom pain, radiculopathy, lumbar pain, visceral pain, bowel pain, and pain associated with osteoarthritis.

Embodiment 22. A method of treatment or prophylaxis of a disease in which Kv1.3 channels are involved in a subject in need thereof, comprising administering a therapeutically effective amount of a compound of formula I, II, III and IV to a subject in need of treatment or prophylaxis of a disease in which Kv1.3 channels are involved.

Embodiment 23. A method of treatment of an autoimmune disease in a subject in need thereof, comprising administering a therapeutically effective amount of a compound of formula I, II, III and IV to a subject having an autoimmune disease.

Embodiment 24. A method of treatment of diabetes or insulin resistance syndromes in a subject in need thereof, comprising administering a therapeutically effective amount of a compound to a subject having diabetes or an insulin resistance syndrome.

Embodiment 25. A method of treatment of epilepsy or seizures in a subject in need thereof, comprising administering a therapeutically effective amount of a compound to a subject having epilepsy or seizures.

Embodiment 26. The method according to embodiments 20 through 23, wherein the compound is administered in a therapeutically effective amount between 0.018 and 1.8 mg/kg.

Embodiment 27. The compound, composition, use, or method disclosed here, wherein the compound is a compound of formula I, wherein
X is O;
Y is CH;
Z is C;
$R^1$ is alkyl;
$R^2$ is —$CH_2$—$R^3$; wherein $R^3$ is —$R^4$-$R^5$; wherein $R^4$ is alkyl and $R^5$ is heteroaryl;
Q is C;
D is C;
A is —$R^6$-$R^7$; wherein $R^6$ is alkyl and $R^7$ is heteroaryl;
E is H; and
J is H.

Embodiment 28. The compounds according to embodiments 1 through 6, wherein the compound is isolated or synthetically produced.

Embodiment 29. The compounds according to embodiments 7 through 28, wherein the compound is nitenin or dihydronitenin.

BRIEF DESCRIPTION OF DRAWINGS

For easier understanding of this application, figures are attached in the annex that represent exemplary forms of implementation which nevertheless are not intended to limit the technique disclosed herein.

a) In sdDRGns, voltage-activated outward potassium ($K^+$) currents were evoked by a depolarizing step to +20 mV (holding potential of −70 mV) preceded by a hyperpolarizing pre-pulse to −120 mV. Currents were better fit by the sum of two exponential functions, thus revealing two components (here termed $I_{slow}$ and $I_{fast}$) whose time constants were $\tau_{fast}$ ~75 ms and $\tau_{slow}$ ~495 ms.

b) i. Typical voltage activated $K^+$ current traces recorded before and in the presence of nitenin (0.1 µg/ml); lower trace corresponding to the current subtraction, fit with a single-exponential function (time constant τ~150 ms). ii. Typical voltage activated $Na^+$ currents recorded before (black line) and in the presence of nitenin (0.1 µg/ml; 0.29 µM) (grey line), showing an absence of effect.

Figure 2:
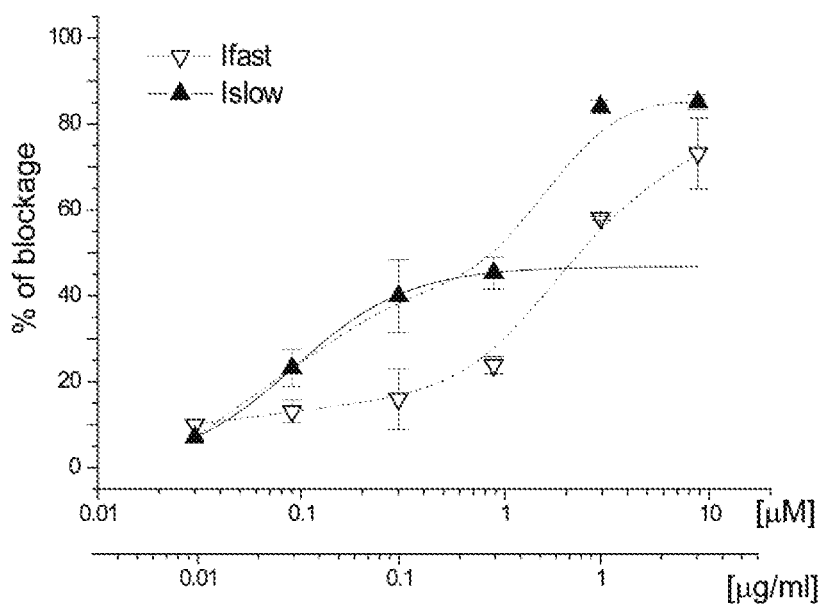
Figure 2:
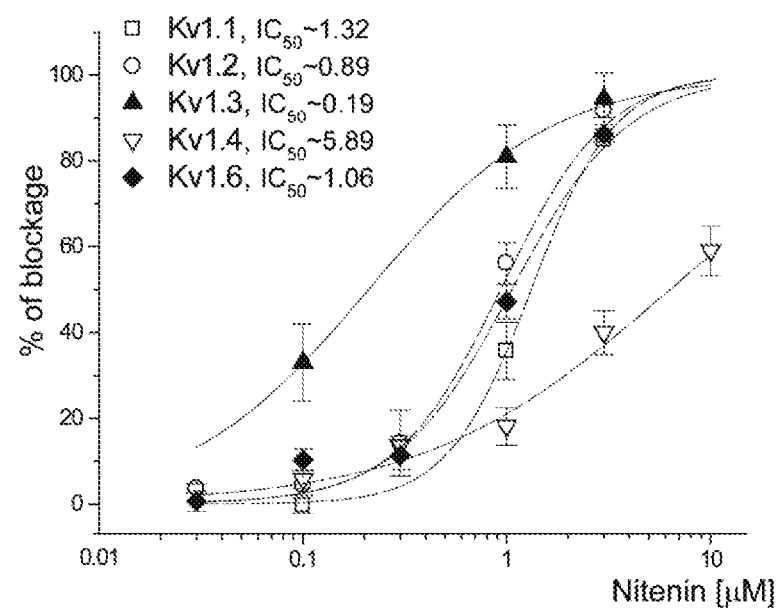

FIG. 2 shows dose dependent responses of nitenin on voltage activated $K^+$ currents recorded from (a) small diameter Dorsal Root Ganglia neurons (sdDRGns) and from (b) CHO-K1 cells expressing human Kv1.1, Kv1.2, Kv1.3, Kv1.4 or Kv1.6 cDNA.

a) Effect of nitenin, as percentage of current blockage, on the fast ($I_{fast}$, open inverted triangles) and slow ($I_{slow}$, filled triangles) current components recorded from sdDRGns, as dose-response relationships. As measure of $I_{fast}$, peak current was used, whereas, as a measure of $I_{slow}$, the current value was obtained at the end of the command pulse (see FIG. 1). Values are expressed as mean±S.E.M. For $I_{slow}$, a dual phase relationship can be observed. Consequently, for the lower concentration values (up to 1 µM) the relationship was fit with a Hill Function, showing an $IC_{50}$ of 120 nM); for concentrations higher than 1 µM, the dose dependence appears to coincide with the dose dependence of $I_{fast}$ ($IC_{50}$ of ~6 µM).

b) Effect of nitenin on $K^+$ currents recorded from CHO-K1 cells stably transfected and expressing hKv1.1, hKv1.2, hKv1.3, hKv1.4 or hKv1.6. Concentration—% blockage values were fit with Hill functions, which IC50 values (in nM) are displayed in the in the Figure. Kv1.3 channel is the most sensitive channel (around 6-fold more sensitive in comparison to the "next most sensitive one", the Kv1.2) Kv1.2, Kv1.1 and Kv1.6 show similar, intermediate sensitivities to nitenin. In opposition, Kv1.4 is the less sensitive (~31 times less sensitive).

Figure 3:
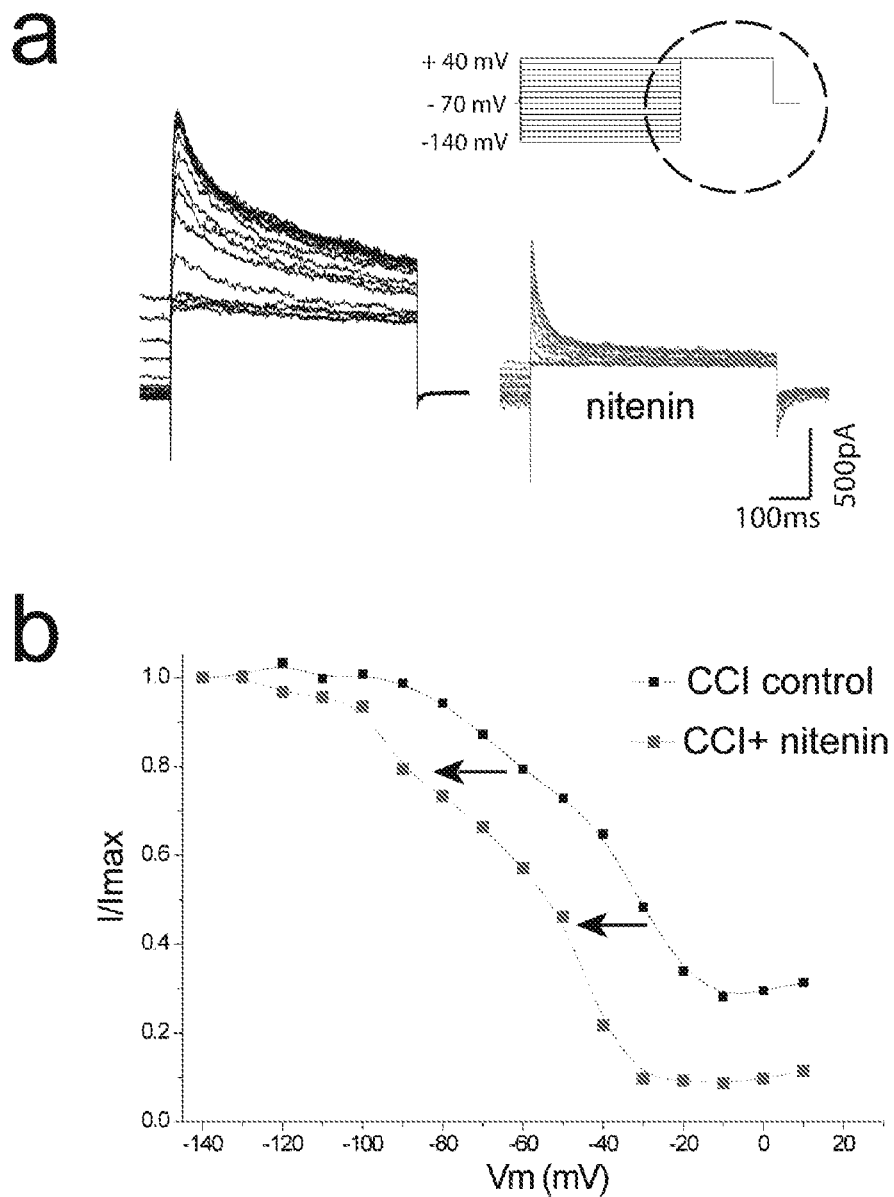

FIG. 3 shows a typical effect of nitenin on the voltage dependence of steady state of inactivation of the $K^+$ currents recorded from a small diameter neuron isolated from a dorsal-root ganglion isolated of the injured side of a CCI rat model 28 days after surgery. a) Current traces were elicited during a command pulse to +10 mV (600 ms) preceded by a series pre-pulses of 11040 s duration, ranging from −140 to +10 mV in a 10 mv step increments; traces in the left (black) were obtained before and those on the right (in grey), during the application of nitenin (0.1 μg/ml; 0.29 μM). b) Current/voltage relationships where current peak amplitudes (obtained in 'a') are plotted against the potentials of the pre-pulse used in the voltage protocol in 'a' (bullets in black relate to control-CCI; bullets in grey, during nitenin treatment). One can observe a shift to hyperpolarized values during the nitenin treatment. The relationships were better fit with the sum of two Boltzmann functions, showing that in both conditions there are two components: one more hyperpolarized component (component 1) and one other more depolarized component (component 2). In fact, the Vh parameters (voltage of half maximum current) of the Boltzmann equation showed more hyperpolarized values when during nitenin treatment (control: Vh1=−73.3 mV Vh2=−26.3 mV; nitenin: Vh1=−95.3 mV Vh2=−47.0 mV).

Figure 4:
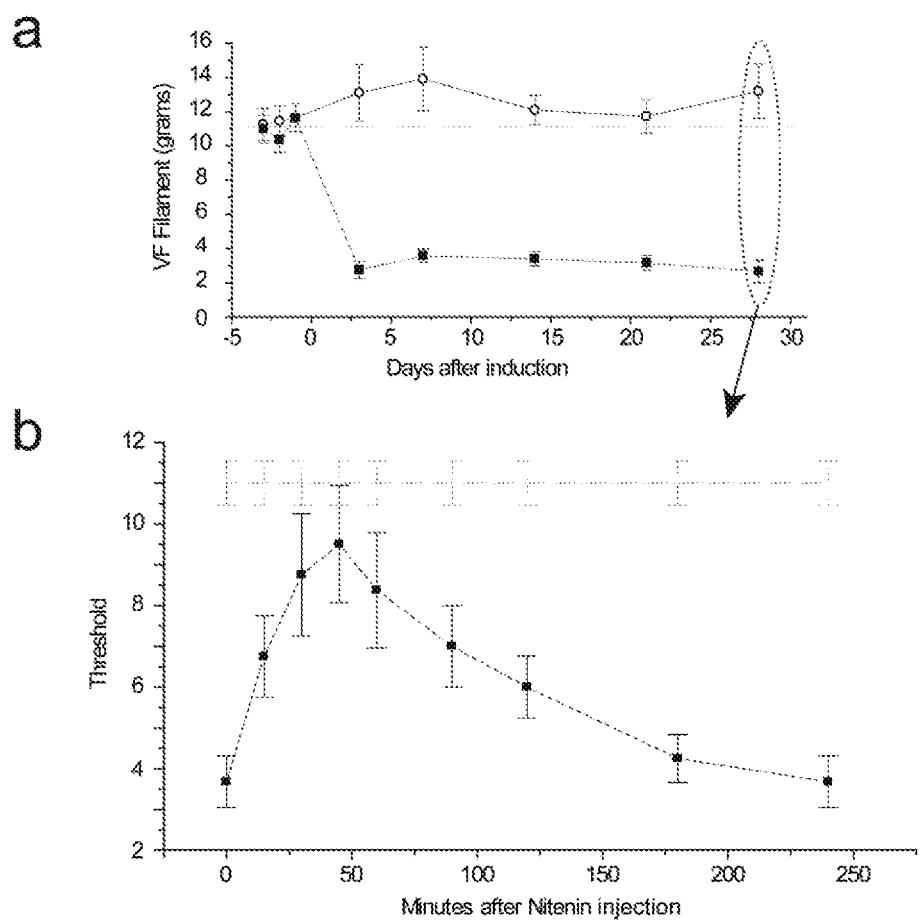

FIG. 4 illustrates behavioral readouts as measures of pain during treatment with nitenin on a Neuropatic pain rat model CCI (Chronic constriction injury). Typical experiment using a group of Wistar rats subjected to four unilateral sciatic nerve constrictions. Values refer to the mechanical sensitivity to stimulation using calibrated von Frey Filaments, and consequently reflecting hyperalgesia when hypersensitive (black filled markers—ipsilateral, operated leg; Open markers—contralateral, uninjured leg). Dotted line refers to the average value of the ipsilateral paw prior to surgery. a) Induction of the model showing that 3 days after operation, the mechanical sensitivity of the ipsilateral limb increases markedly, whereas the one associated with the contralateral leg remained unchanged, similar to baseline values. This tendency is maintained during 26 days after surgery, day that treatment with nitenin was performed (circle with dotted line). b) Effect of intravenous injection of nitenin (estimated plasma concentration of 1 μg/ml) on the mechanical sensitivity of the ipsilateral leg. For clarity, the data of the contralateral limb is not shown but it remains unaltered. The effect is maximum at around ~1 h after injection, reaching values not different to those obtained during baseline, prior to surgery (values in doted lines).

Figure 5:
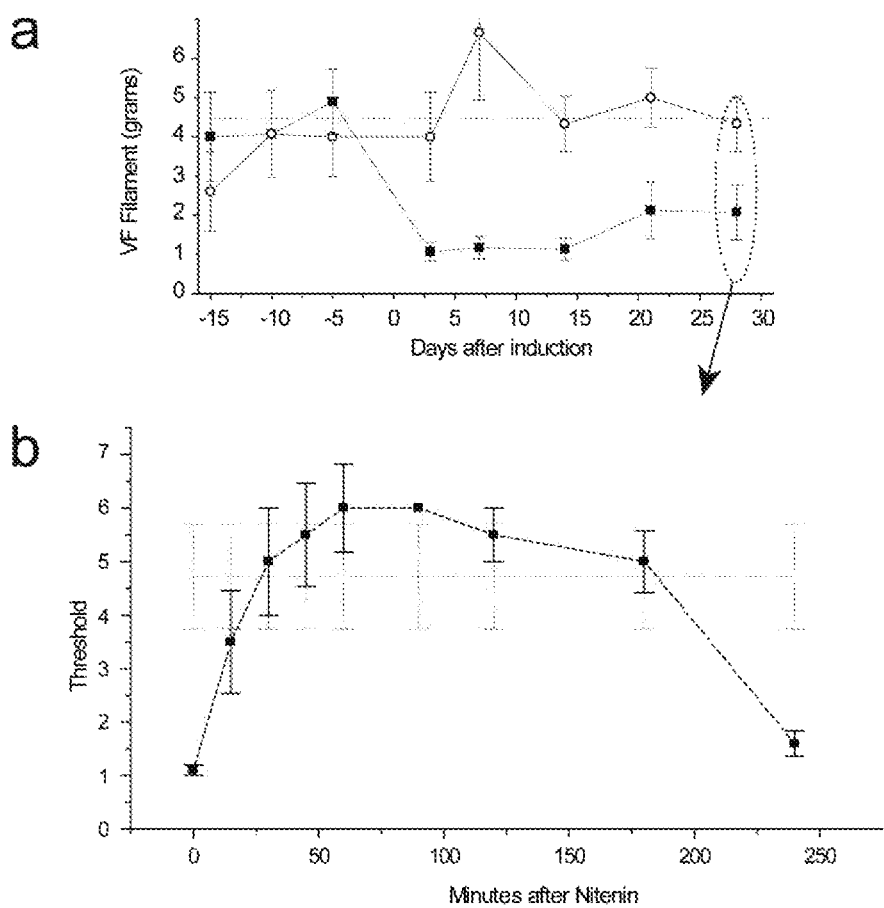

FIG. 5 shows behavioral readouts as measures of pain during treatment with nitenin on an Orofacial pain rat model; Typical experiment using a group of Wistar rats subjected to injection of CFA (CFA was injected just posterior to the second row of vibrissae). Values refer to the mechanical sensitivity to face stimulation (whiskers region) using calibrated von Frey Filaments, and consequently reflecting hyperalgesia when hypersensitive (black filled markers—ipsilateral, injured face-side; Open markers—contralateral, uninjured face-side). Dotted line refers to the average value of the ipsilateral face prior to the CFA injection. a) Induction of the model showing that 3 days after operation, the mechanical sensitivity of the ipsilateral face-sides increase markedly, whereas the one associated with the contralateral leg maintains relatively unchanged, similar to baseline values. This tendency in maintained during 26 days after induction, day that treatment with nitenin was performed (circle with dotted line). b) Effect of intravenous injection of nitenin (estimated plasma concentration of 1 μg/ml) on the mechanical sensitivity of the ipsilateral face-side. For clarity, the data of the contralateral face-side is not shown but it remains relatively unaltered. The effect is maximum at around ~1 to 2 h after nitenin injection, reaching values not different to those obtained during baseline, prior to induction (values in doted lines), but in cases higher.

Figure 1:
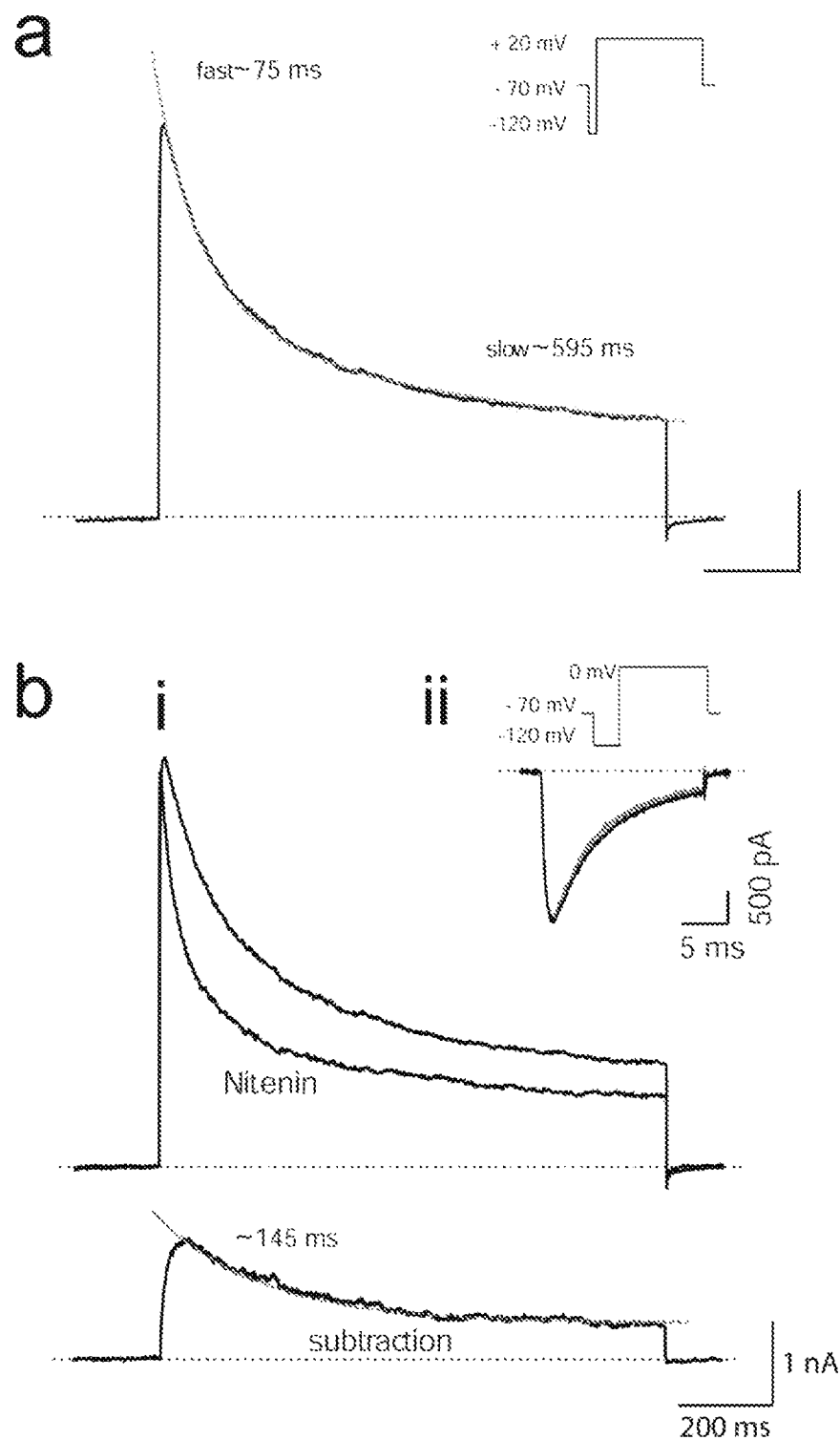
FIG. 1 illustrates the effect of nitenin (0.1 µg/ml) on voltage activated currents recorded from small diameter Dorsal Root Ganglia neurons (sdDRGns)
Figure 6:
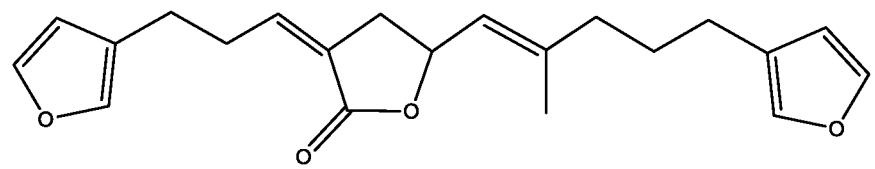
Figure 6:
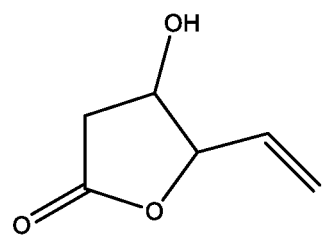
Figure 6:
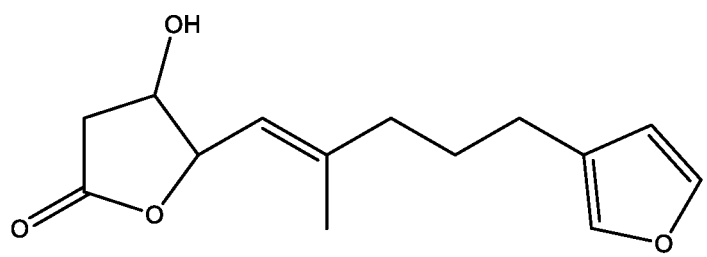
Figure 6:
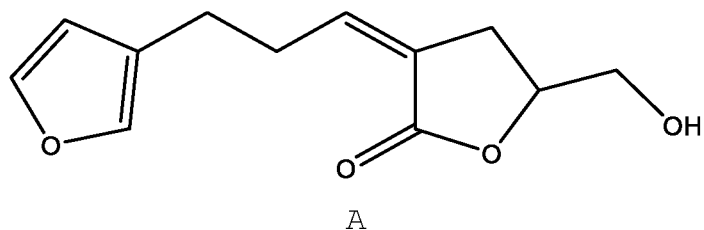
Figure 6:
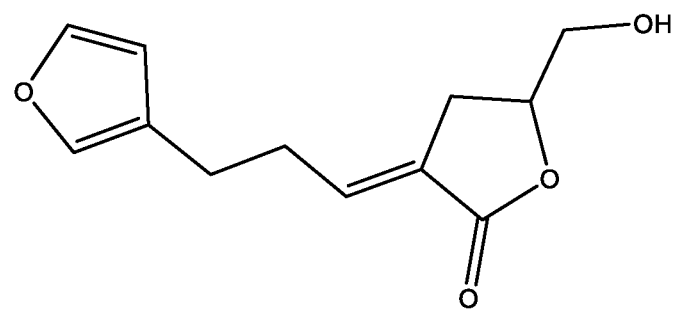

FIG. 6 illustrates the formulas of 4 of the compounds tested where the compound of formula V refers to nitenin (results on ionic currents are presented in FIGS. 1, 2 and 3, and, the in vivo efficacy, in FIGS. 4 and 5). Formulas is VIII.A and VIII.B represent the Cis-isomer and Trans-isomer, respectively, of the compound of formula VIII.

Figure 7:
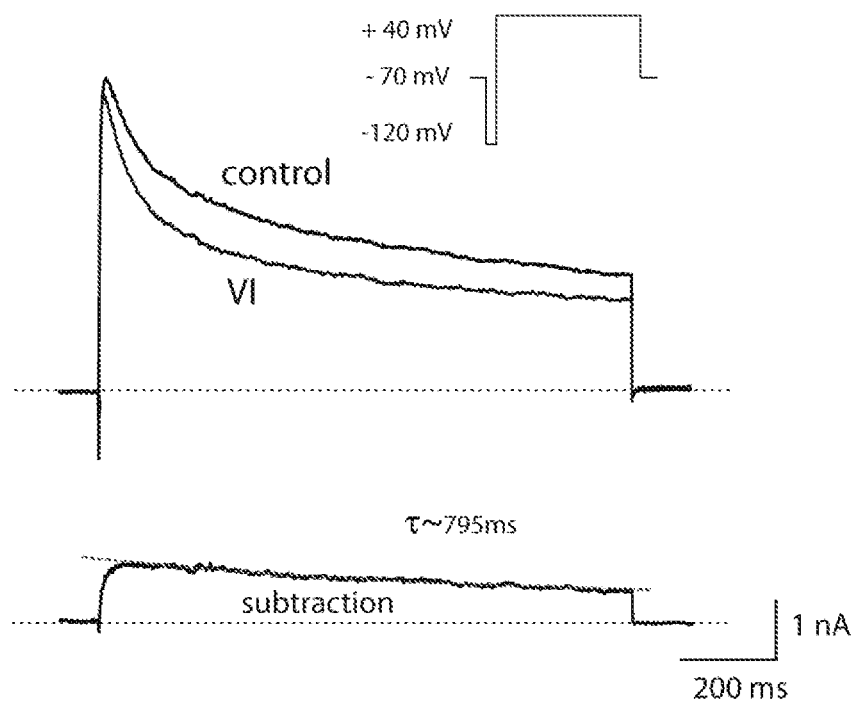

FIG. 7 illustrates the effect of the compound of formula VI (10 μg/ml; 77.9 μM) on voltage activated currents recorded sdDRGns. Typical voltage activated $K^+$ current traces recorded before and in the presence of the compound of formula VI (10 μg/ml; 77.9 μM); lower trace corresponding to the current subtraction, fit with a single-exponential function (time constant τ~795 ms).

Figure 8:
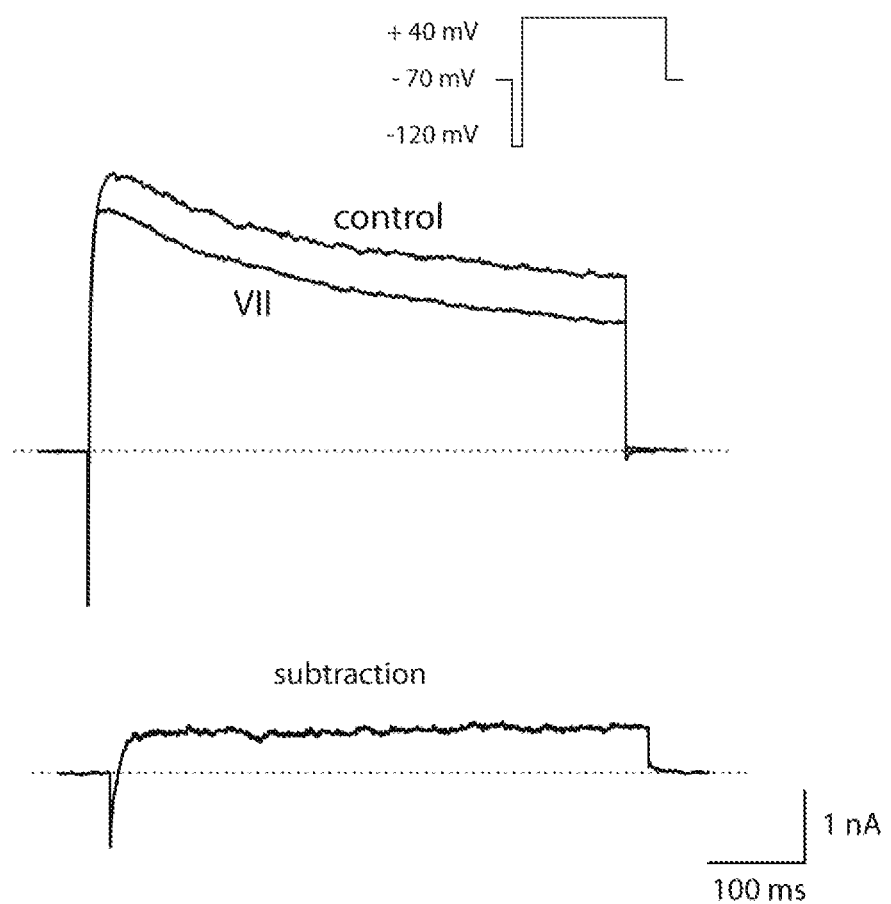

FIG. 8 illustrates the effect of the compound of formula VII (0.1 μg/ml; 399 nM) on voltage activated currents recorded sdDRGns. Typical voltage activated $K^+$ current traces recorded before and in the presence of the compound of formula VII (0.1 μg/ml; 399 nM); lower trace corresponding to the current subtraction.

Figure 9:
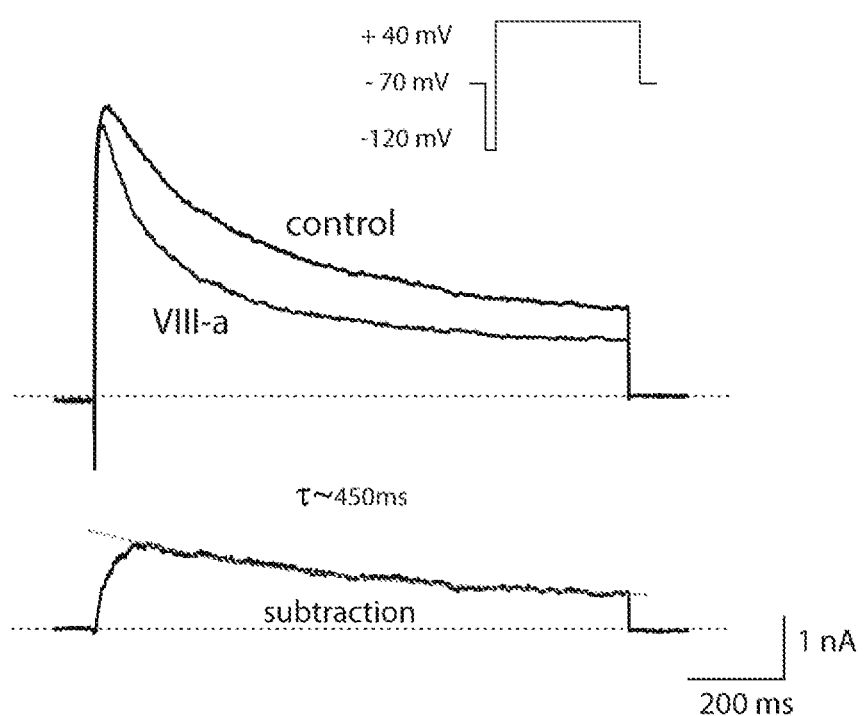

FIG. 9 illustrates the effect of the compound of formula VIII-A (6.5 μg/ml; 29.4 μM) on voltage activated currents recorded sdDRGns. Typical voltage activated $K^+$ current traces recorded before and in the presence of the compound of formula VIII-A (6.5 μg/ml; 29.4 μM); lower trace corresponding to the current subtraction, fit with a single-exponential function (time constant τ~450 ms).

Figure 10:
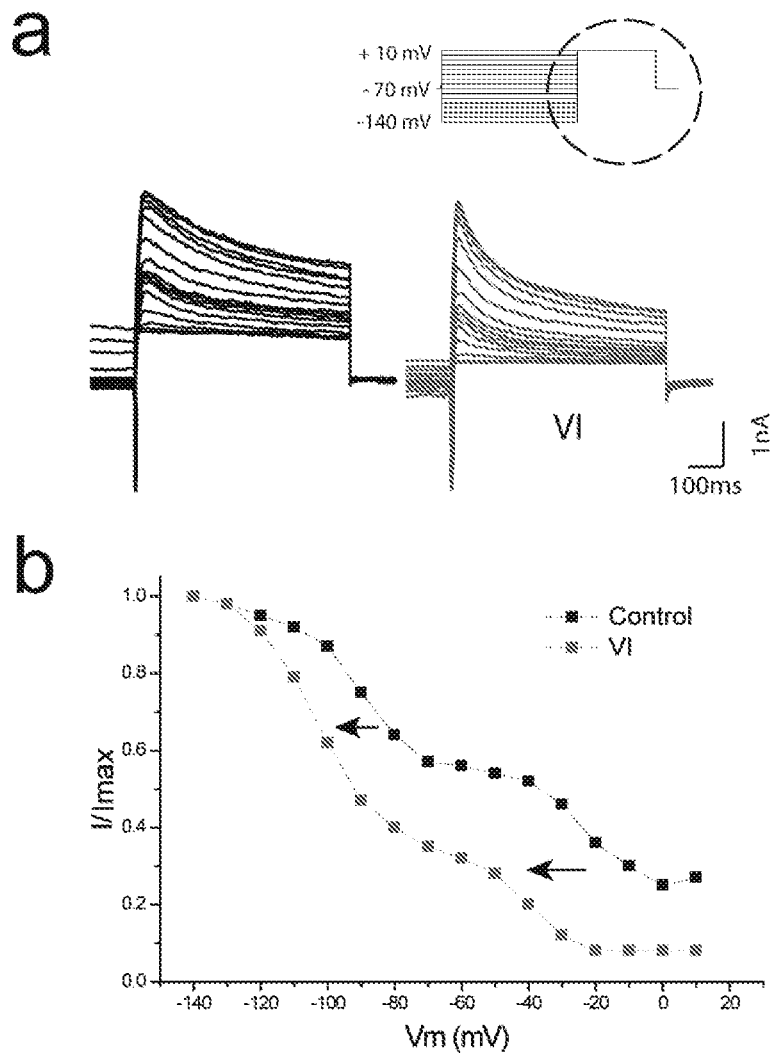

FIG. 10 shows a typical effect of the compound of formula VI on the voltage dependence of steady state of inactivation of the $K^+$ currents recorded from a sdDRGn. a) Current traces were elicited during a command pulse to +10 mV (600 ms) preceded by a series pre-pulses of 11040 s duration, ranging from −140 to +10 mV in a 10 mv step increments; traces in the left (black) were obtained before and those on the right (in grey), during the application of the compound of formula VI (10 μg/ml; 77.9 μM). b) Current/voltage relationships where current peak amplitudes (obtained in 'a') are plotted against the potentials of the pre-pulse used in the voltage protocol in 'a' (bullets in black relate to control-CCI; bullets in grey, during treatment with the compound of formula VI). One can observe a shift to hyperpolarized values during the treatment with the compound of formula VI. The relationships were better fit with the sum of two Boltzmann functions, showing that in both conditions there are two components: one more hyperpolarized component (component 1) and one other more depolarized component (component 2). In fact, the Vh parameters (voltage of half maximum current) of the Boltzmann equation showed more hyperpolarized values when during F2 treatment (control: Vh1=−91.0 mV Vh2=−23.9 mV; F2: Vh1=−102.9 mV Vh2=−40.5 mV).

Figure 11:
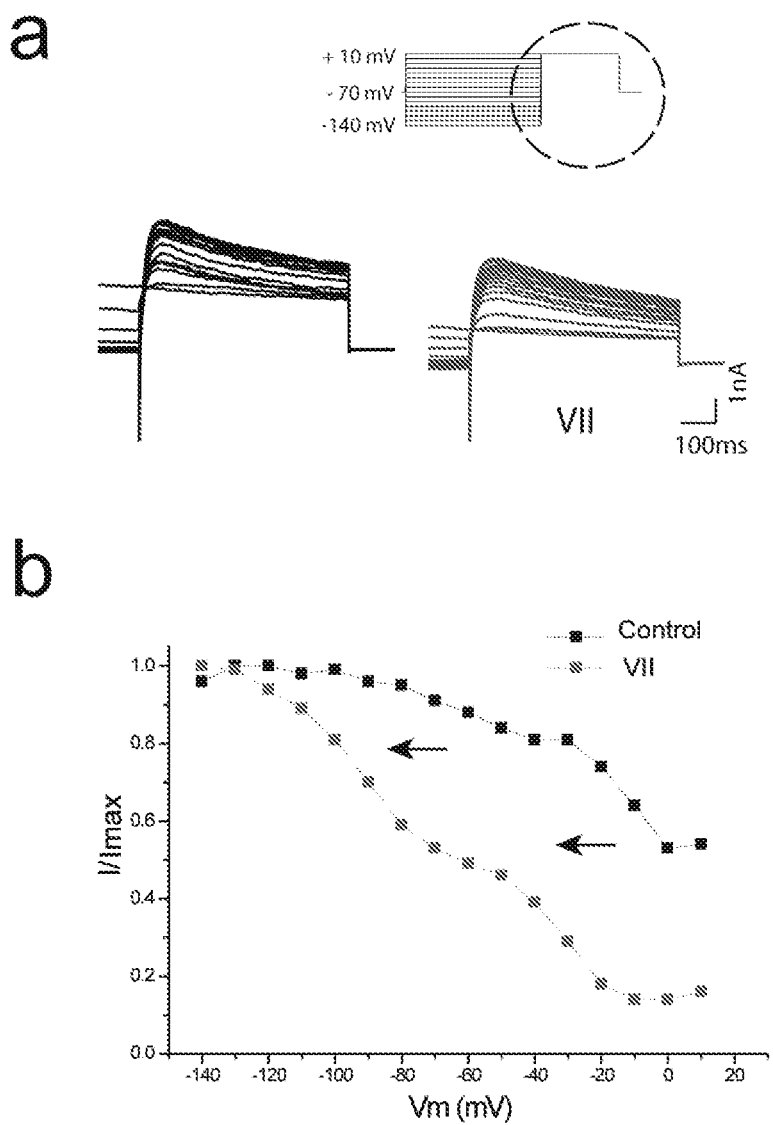

FIG. 11 shows a typical effect of the compound of formula VII on the voltage dependence of steady state of inactivation of the $K^+$ currents recorded from a sdDRGn. a) Current traces were elicited during a command pulse to +10 mV (600 ms) preceded by a series pre-pulses of 11040 s duration, ranging from −140 to +10 mV in a 10 mv step increments; traces in the left (black) were obtained before and those on the right (in grey), during the application of F3 (0.1 μg/ml; 399 nM). b) Current/voltage relationships where current peak amplitudes (obtained in 'a') are plotted against the potentials of the pre-pulse used in the voltage protocol in 'a' (bullets in black relate to control-CCI; bullets in grey, during treatment with the compound of formula VII). One can observe a shift to hyperpolarized values during the treatment with the compound of formula VII. The relationships were better fit with the sum of two Boltzmann functions, showing that in both conditions there are two components: one more hyperpolarized component (component 1) and one other more depolarized component (component 2). In fact, the Vh parameters (voltage of half maximum current) of the Boltzmann equation showed more hyperpolarized values when during treatment with the compound of formula VII (control: Vh1=−64.1 mV Vh2=−13.7 mV; F2: Vh1=−92.6 mV Vh2=−32.4 mV).

Figure 12:
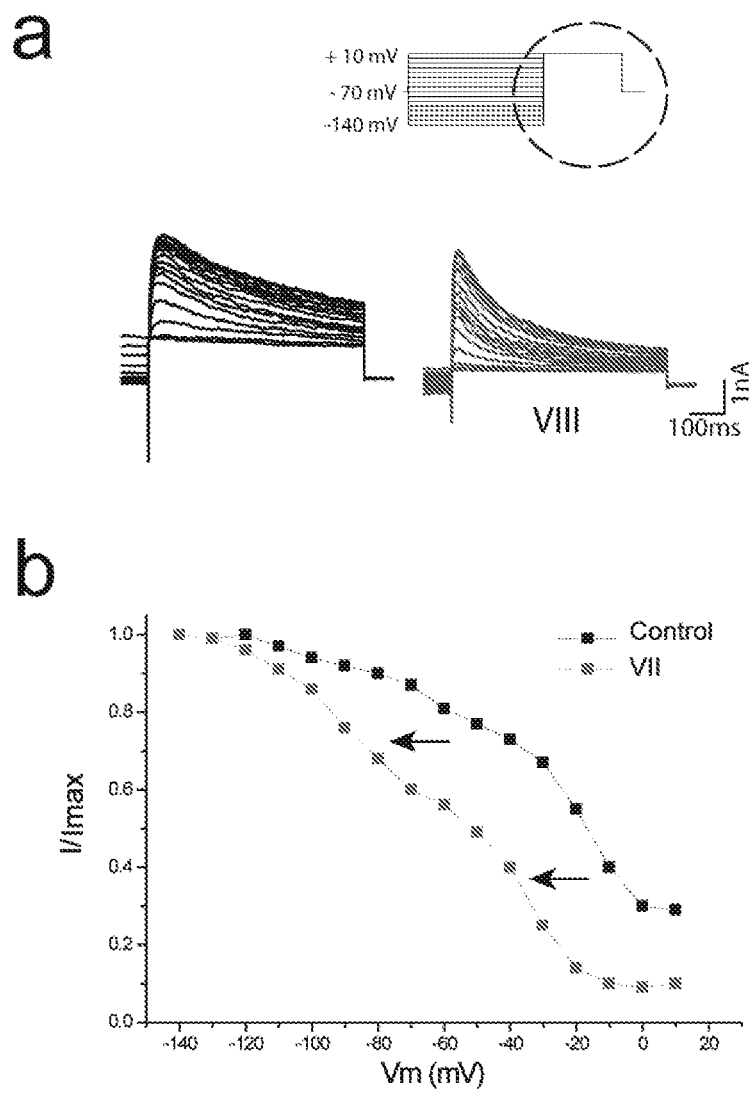

FIG. 12 shows a typical effect of the compound of formula VIII-A on the voltage dependence of steady state of inactivation of the $K^+$ currents recorded from a sdDRGn. a) Current traces were elicited during a command pulse to +10 mV (600 ms) preceded by a series pre-pulses of 11040 s duration, ranging from −140 to +10 mV in a 10 mv step increments; traces in the left (black) were obtained before and those on the right (in grey), during the application of the compound of formula VIII (6.5 µg/ml; 29.4 µM). b) Current/voltage relationships where current peak amplitudes (obtained in 'a') are plotted against the potentials of the pre-pulse used in the voltage protocol in 'a' (bullets in black relate to control-CCI; bullets in grey, during treatment with the compound of formula VIII). One can observe a shift to hyperpolarized values during the treatment with the compound of formula VIII. The relationships were better fit with the sum of two Boltzmann functions, showing that in both conditions there are two components: one more hyperpolarized component (component 1) and one other more depolarized component (component 2). In fact, the Vh parameters (voltage of half maximum current) of the Boltzmann equation showed more hyperpolarized values when during treatment with the compound of formula VIII (control: Vh1=−53.6 mV Vh2=−18.1 mV; F2: Vh1=−88.9 mV Vh2=−35.5 mV).

DETAILED DESCRIPTION

As used in this application, except as otherwise expressly provided herein, each of the following terms shall have the meaning set forth below. Additional definitions are set forth throughout the application.

References to compounds of the disclosure, or pharmaceutically acceptable salts and prodrugs thereof, ninetin, and ninetin analogues, are used herein interchangeably. The terms include all stereoisomers of these compounds.

The term "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone). It is understood that wherever aspects are described herein with the language "comprising," otherwise analogous aspects described in terms of "consisting of" and/or "consisting essentially of" are also provided.

Unless defined otherwise, all technical and scientific terms used herein have the same meaning as commonly understood by one of ordinary skill in the art to which this disclosure is related.

Units, prefixes, and symbols are denoted in their Systeme International de Unites (SI) accepted form. Numeric ranges are inclusive of the numbers defining the range. The headings provided herein are not limitations of the various aspects of the disclosure, which can be had by reference to the specification as a whole. Accordingly, the terms defined immediately below are more fully defined by reference to the specification in its entirety.

"Administering" refers to the physical introduction of an agent to a subject, using any of the various methods and delivery systems known to those skilled in the art. Exemplary routes of administration for the compounds disclosed herein include intravenous, intramuscular, subcutaneous, intraperitoneal, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intralymphatic, intralesional, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion, as well as in vivo electroporation. In some embodiments, the compound is administered via a non-parenteral route, e.g., orally. Other non-parenteral routes include a topical, epidermal or mucosal route of administration, for example, intranasally, vaginally, rectally, sublingually or topically. Administering can also be performed, for example, once, a plurality of times, and/or over one or more extended periods.

The term "isolated" means purified from nature and thus free from the natural compounds that exist with nitenin in its natural environment and it associates with in nature. Isolated products of nature may have different chemical, biochemical, and/or physical properties than the same product as it exists in nature. Synthetic versions of products of nature may have different chemical, biochemical, and/or physical properties than the same product isolated from nature or as it exists in nature.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. Drug-approval agencies (e.g., EMA, US-FDA) provide guidance and approve pharmaceutically acceptable compounds, materials, compositions, and/or dosage forms. Examples are listed in, for example, Pharmacopeias.

The phrases "pharmaceutically acceptable excipient" and "pharmaceutically acceptable carrier" are employed herein to refer to a pharmaceutically acceptable material chosen from a solvent, dispersion media, diluent, dispersion, suspension aid, surface active agent, isotonic agent, thickening or emulsifying agent, preservative, polymer, peptide, protein, cell, hyaluronidase, and mixtures thereof. In some embodiments, the solvent is an aqueous solvent.

A "therapeutically effective amount," "effective dose," or "effective amount," of a drug or therapeutic agent is any amount of the drug that, when used alone or in combination with another therapeutic agent, protects a subject against the onset of a disease or promotes disease regression evidenced by a decrease in severity of disease symptoms, an increase in frequency and duration of disease symptom-free periods, or a prevention of impairment or disability due to the disease affliction. The ability of a therapeutic agent to promote disease regression can be evaluated using a variety of methods known to the skilled practitioner, such as in human subjects during clinical trials, in animal model systems predictive of efficacy in humans, or by assaying the activity of the agent in in vitro assays.

In one embodiment, the "therapeutically effective dosage" is the dosage whose administration, either in a single dose or multiple dose schedule, is effective for treatment, prevention and/or reduction of pain. This dosage varies depending upon the health and physical condition of the individual to be treated, age, degree of analgesia desired, and other relevant factors. It is expected that the amount will fall in a relatively broad range that can be determined through routine trials. "Preventing" or "prevention" herein does not require absolute success in the sense of an absolute prevention of pain but indicates a reduced risk of developing a painful condition or developing pain with reduced severity. Likewise, "treatment" shall not be construed as an absolute cure, but may also relate to amelioration or suppression of pain or pain associated conditions.

The terms "alkyl," "alkyl unit," and "alkyl group" as used interchangeably herein refer to a saturated monovalent hydrocarbon radical comprising one to twelve carbon atoms (C1-C12). Alkyl groups may be linear, branched, or cyclic. Alkyl groups may be unsubstituted, or they may be substituted as described elsewhere herein. In some embodiments, an alkyl group comprises one to eight carbon atoms (C1-C8). In some embodiments, an alkyl group comprises one to six carbon atoms (C1-C6). In some embodiments, an alkyl group comprises one to four carbon atoms (C1-C4). In some embodiments, a cyclic alkyl group comprises three to six carbon atoms (C3-C6).

The terms "alkenyl," "alkenyl unit," and "alkenyl group" as used interchangeably herein refer to a monovalent hydrocarbon radical comprising two to eight carbon atoms (C2-C8) with at least one site of unsaturation (i.e., an sp2 carbon-carbon double bond). Alkenyl groups may be linear, branched, or cyclic. Alkenyl groups may be unsubstituted, or they may be substituted as described elsewhere herein. In some embodiments, an alkenyl group comprises two to six carbon atoms (C2-C6). In some embodiments, an alkenyl group comprises two to four carbon atoms (C2-C4). Alkenyl groups may have E or Z orientations. Non-limiting examples of alkenyl groups include ethenyl (also called vinyl), 1-propenyl, iso-propenyl, and 2-chloroethenyl.

The terms "aryl," "aryl unit," and "aryl group" as used interchangeably herein refer to a monovalent aromatic hydrocarbon radical comprising 6-20 carbon atoms (C6-C20) that is derived by removing a hydrogen atom from an aromatic ring. Aryl groups can be unsubstituted, or they can substituted with one or more substituents as described elsewhere herein.

The terms "heterocycle," "heterocyclyl," "heterocyclic unit," and "heterocyclic group" as used interchangeably herein refer to a saturated or partially unsaturated ring system comprising 3 to 20 atoms, wherein at least one of the ring atoms is a heteroatom chosen from nitrogen, oxygen, phosphorous, and sulfur. A heterocyclic group may be unsubstituted or may be substituted with one or more substituents as described elsewhere herein. In some embodiments, a heterocyclic group comprises 3 to 10 atoms. In some embodiments, a heterocyclic group comprises 3 to 7 atoms. In some embodiments, a heterocyclic group is monocyclic. In some embodiments, a heterocyclic group is bicyclic. In some embodiments, a heterocyclic group comprises fused rings.

The terms "heteroaryl," "heteroaryl unit," and "heteroaryl group" as used interchangeably herein refer to a monovalent aromatic radical comprising one or more 5-, 6-, or 7-membered rings and comprising one or more heteroatoms independently chosen from nitrogen, oxygen, phosphorous, and sulfur. A heteroaryl group may be unsubstituted or may be substituted with one or more substituents as described elsewhere herein. In some embodiments, a heteroaryl group comprises 5 to 20 atoms. In some embodiments, a heteroaryl group comprises 5 to 9 atoms. In some embodiments, a heteroaryl group comprises 5 atoms. In some embodiments, a heteroaryl group comprises 6 atoms. In some embodiments, a heteroaryl group comprises atoms. In some embodiments, a heteroaryl group is monocyclic. In some embodiments, a heteroaryl group is bicyclic. In some embodiments, a heteroaryl group comprises fused rings.

The term "substituted" as used herein refers to the replacement of one or more hydrogen atoms or one or more of a hydrocarbon radical, alkyl group, alkylene group, alkenyl group, alkenylene group, alkynyl group, alkynylene group, aryl group, heterocyclic group, or heteroaryl group with one or more substituents. On a substituted hydrocarbon radical, alkyl group, alkylene group, alkenyl group, alkenylene group, alkynyl group, alkynylene group, aryl group, heterocyclic group, or heteroaryl group, any number of hydrogen atoms may be replaced by substituents.

Compounds of the disclosure may contain one or more chiral centers. Compounds of the disclosure thus may exist in different stereoisomeric forms. It is intended that all stereoisomeric forms of the compounds described herein, including, as non-limiting examples, diastereomers, enantiomers, and mixtures thereof (including, as a non-limiting example, racemic mixtures) form parts of the disclosure.

Abbreviations:
$Ca^{2+}$: Calcium
$Ca_V$: Voltage-gated calcium channel
CCI: Chronic Constriction Injury
CFA: Complete Freund's Adjuvant
CHO: Chinese hamster ovary
CIPN: Chemotherapy-induced Peripheral Neuropathy
CNS: Central nervous system
COP: Chronic orofacial pain
DRG: Dorsal root ganglion
ECG: Electrocardiogram
HEK: Human embryonic kidney
hERG: Human Ether-à-go-go-Related Gene—Kv11.1
HFF2: Human foreskin fibroblasts 2
I: current
$I_{fast}$: Fast current component
$I_{slow}$: Slow current component
IV: Intravenous
$K^+$: Potassium
$K_V$: voltage-dependent potassium channel
$K_V1.x$: voltage-dependent potassium channel subunits, given by x
L: Lumbar
Nat: Sodium
$Na_V$: Voltage-gated sodium channel
$Na_V1.x$: voltage-dependent sodium channel subunits, given by x
NSAID(s): non-steroidal anti-inflammatory drug(s)
MTS: (3-(4,5-dimethylthiazol-2-yl)-5-(3-carboxymethoxyphenyl)-2-(4-sulfophenyl)-2H-tetrazolium)
sdDRGN: small diameter dorsal root neurons
sdTGN: small diameter trigeminal ganglion neurons
STZ: Streptozotocin
TG: Trigeminal Ganglion
TRP: Transient Receptor Potential Cation channel
TRPV1: Transient Receptor Potential Cation channel subfamily
USA: United States of America V member 1

V: Voltage

Vh: Voltage of half maximum current

Compounds of the disclosure, pharmaceutically acceptable salts of said compounds, and/or pharmaceutical compositions comprising said compounds and/or pharmaceutically acceptable salts thereof can be administered as therapeutic treatments. Said compounds, pharmaceutically acceptable salts, and/or pharmaceutical compositions can be administered in unit forms of administration to mammalian subjects, including human beings. Suitable unit forms of administration include, as non-limiting examples, forms administered orally and forms administered via a parenteral route, non-limiting examples of which including inhalation, subcutaneous administration, intramuscular administration, intravenous administration, intradermal administration, and intravitreal administration.

In some embodiments, pharmaceutical compositions for oral administration can be in the form of tablets, pills, powders, hard gelatine capsules, soft gelatine capsules, and/or granules. In some embodiments of such pharmaceutical compositions, a compound of the disclosure and/or a pharmaceutically acceptable salt of a compound of the disclosure is (or are) mixed with one or more inert diluents, non-limiting examples of which including starch, cellulose, sucrose, lactose, and silica. In some embodiments, such pharmaceutical compositions may further comprise one or more substances other than diluents, such as (as non-limiting examples), lubricants, coloring agents, coatings, or varnishes.

The pharmaceutical compositions of the disclosure may comprise pharmaceutically acceptable carriers, excipients, vehicles, and diluents. Many of these are well-known to persons having ordinary skill in the art and are described in, as a non-limiting example, *Remington: The Science and Practice of Pharmacy, 22nd Edition*, Lippincott Williams & Wilkins, Philadelphia, Pa. (2013) and any other editions, which are hereby incorporated by reference.

In one aspect, this disclosure relates to nitenin analogue compounds and their use as analgesics for the treatment, prevention or reduction of chronic and acute pain. Through an approach using physiology and pharmacology of ionic currents/channels, a novel pharmaceutical application regarding an analgesic effect for several types of pain is disclosed herein.

In sharp contrast to the existing therapeutic drugs, the analgesic compound disclosed herein will be positioned as a breakthrough in pain management due to its novel mode of action, and predicted effectiveness in humans, target specificity, and reduced side-effects. Nitenin and dihydronitenin compounds (two of the compounds disclosed herein) have their origin in a marine sponge, but have been, and can be, synthetically prepared for this disclosure and the disclosure provides that these compounds act specifically on certain $K_V$ channels $K_v1.x$, expressed in the pain-sensing c-fibers of the dorsal root ganglia and of the trigeminal ganglia. Without being bound by theory, it is proposed that the mode of action involves a particular channel inhibition (rather than potentiation, like Retigabine) and has advantageous particularities, such as: (a) it is an "open channel blocker", thus an activity dependent blockage, (b) involves a change of the voltage-dependence of inactivation of the channel, and, (c) acts specifically on a set of $K_V$ channels, mainly Kv1.3. This specific and novel mode of action explains why and how nitenin and nitenin analogue compounds are solely effective in body limbs/body parts with injured/affected nerves. Additionally, it does not alter nociceptive and sensorial scores, in unaffected body limbs/body parts.

In one embodiment, the disclosure relates to the use of nitenin analogue compounds as analgesics for the treatment, prevention or reduction of chronic and acute pain. Thus, in some aspects of the present disclosure the compounds referred to as "nitenin analogue compounds" are illustrated by the compounds of formula I, II, III and IV as described in the following embodiments:

Embodiment 1. Compounds of formula I, II, III and IV, pharmaceutically acceptable salts or prodrug thereof,

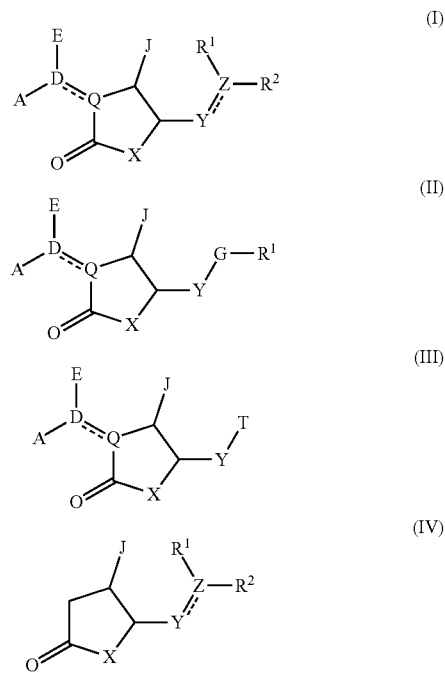

wherein

═ represents a carbon-carbon single bond or a carbon-carbon double bond;

X is selected from O, S, NH, CH$_2$;

Y is selected from CH, CH$_2$;

Z is selected from C, N;

G is selected from O, S;

T is selected from OH, SH, NH$_2$, halogen;

$R^1$ and $R^2$ are independently selected from H, alkyl, alkenyl, cycloalkyl, aryl or —CH$_2$—R$^3$; wherein R$^3$ is selected from aryl, cycloalkyl, heteroaryl, —R$^4$-R$^5$; wherein R$^4$ is selected from alkyl, alkenyl; wherein R$^5$ is selected from aryl, substituted or unsubstituted heteroaryl, substituted or unsubstituted gama-lactone;

Q is selected from C, CH;

D is selected from C, CH, CH$_2$;

One of A and E is H and the other is selected from H, OH, SH, aryl, alkyl, alkenyl, R$^6$—R$^7$, wherein R$^6$ is selected from alkyl, alkenyl, and R$^7$ is selected from alkyl, alkenyl, substituted or unsubstituted aryl, substituted or unsubstituted heteroaryl, substituted or unsubstituted gama-lactone; optionally, wherein the compound is not nitenin, dihydronitenin nor their respective isomers, enantiomers and stereoisomers; and/or, optionally, wherein R7 is not furan-3-yl;

J is selected from H, OH, SH, NH$_2$, halogen.

Embodiment 2. The compounds of formula IV according to embodiment 1, wherein
X is O;
Y is CH;
Z is C;
$R^1$ is H;
$R^2$ is H; and
J is OH.

Embodiment 3. The compounds of formula IV according to embodiment 1, wherein
X is O;
Y is CH;
Z is C;
$R^1$ is alkyl;
$R^2$ is —$CH_2$—$R_3$; wherein $R^3$ is —$R^4$-$R^5$; wherein $R^4$ is alkyl and $R^5$ is heteroaryl J is OH.

Embodiment 4. The compounds of formula II according to embodiment 1, wherein
X is O;
Y is $CH_2$;
G is O;
$R^1$ is H;
J is H;
Q is C;
D is C;
E is H;
A is —$R^6$-$R^7$; wherein $R^6$ is alkyl and $R^7$ is heteroaryl.

Embodiment 5. The compounds of formula II according to embodiment 1, wherein
X is O;
Y is $CH_2$;
G is O;
$R^1$ is H;
J is H;
Q is C;
D is C;
E is —$R^6$-$R^7$; wherein $R^6$ is alkyl and $R^7$ is heteroaryl;
A is H.

Embodiment 6. The compounds of formula I, II, III and IV, according to embodiment 1, wherein $R^7$ is not furan-3-yl.

Embodiment 7. Compounds of formula I, II, III and IV, pharmaceutically acceptable salts or prodrug thereof,

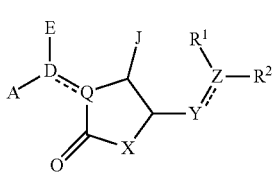
(I)

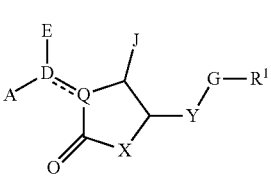
(II)

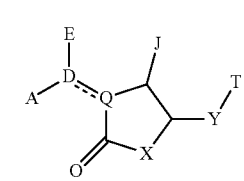
(III)

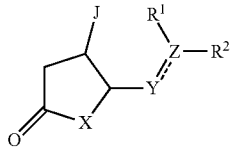
(IV)

wherein
═ represents a carbon-carbon single bond or a carbon-carbon double bond;
X is selected from O, S, NH, $CH_2$;
Y is selected from CH, $CH_2$;
Z is selected from C, N;
G is selected from O, S;
T is selected from OH, SH, $NH_2$, halogen;
$R^1$ and $R^2$ are independently selected from H, alkyl, alkenyl, cycloalkyl, aryl or —$CH_2$—$R^3$; wherein $R^3$ is selected from aryl, cycloalkyl, heteroaryl, —$R^4$-$R^5$; wherein $R^4$ is selected from alkyl, alkenyl; wherein $R^5$ is selected from aryl, substituted or unsubstituted heteroaryl, substituted or unsubstituted gama-lactone;
Q is selected from C, CH;
D is selected from C, CH, $CH_2$;
One of A and E is H and the other is selected from H, OH, SH, aryl, alkyl, alkenyl, $R^6$-$R^7$, wherein $R^6$ is selected from alkyl, alkenyl, and $R^7$ is selected from alkyl, alkenyl, substituted or unsubstituted aryl, substituted or unsubstituted heteroaryl, substituted or unsubstituted gama-lactone;
J is selected from H, OH, SH, $NH_2$, halogen;
for use as a pharmaceutical ingredient.

Embodiment 8. The compounds of formula I for use as pharmaceutical ingredient according to embodiment 7, wherein;
X is O;
Y is CH;
Z is C;
$R^1$ is alkyl;
$R^2$ is —$CH_2$—$R^3$; wherein $R^3$ is —$R^4$-$R^5$; wherein $R^4$ is alkyl and R5 is heteroaryl;
Q is C;
D is C;
A is —$R^6$-$R^7$; wherein $R^6$ is alkyl and $R^7$ is heteroaryl;
E is H; and
J is H.

Embodiment 9. The compounds of formula IV for use as pharmaceutical ingredient according to embodiment 7, wherein;
X is O;
Y is CH;
Z is C;
$R^1$ is H;
$R^2$ is H; and
J is OH.

Embodiment 10. The compounds of formula IV for use as pharmaceutical ingredient, wherein;
X is O;
Y is CH;
Z is C;
$R^1$ is alkyl;
$R^2$ is —CH2-R3; wherein $R^3$ is —$R^4$-$R^5$; wherein $R^4$ is alkyl and $R^5$ is heteroaryl J is OH.

Embodiment 11. The compounds of formula II for use as pharmaceutical ingredient according to embodiment 7, wherein;

X is O;
Y is CH$_2$;
G is O;
R$^1$ is H;
J is H;
Q is C;
D is C;
E is H;
A is —R$^6$-R$^7$; wherein R$^6$ is alkyl and R$^7$ is heteroaryl.

Embodiment 12. The compounds of formula II for use as pharmaceutical ingredient according to embodiment 7, wherein;
X is O;
Y is CH$_2$;
G is O;
R$^1$ is H;
J is H;
Q is C;
D is C;
E is —R$^6$-R$^7$; wherein R$^6$ is alkyl and R$^7$ is heteroaryl;
A is H.

Embodiment 13. For pharmaceutical use, the compounds of formula I, II, III and IV, of the present patent application is used in warm-blooded vertebrates, preferably mammals, more preferably humans, in doses ranging from 0.1 μg/ml blood (6 μg/Kg body weight) to 30 μg/ml blood (1.8 mg/Kg body weight). The previously-mentioned effective dose range is for intravenous administration and it may differ in other routes of administration.

Embodiment 14. The compounds of formula I, II, III and IV pharmaceutical salts or prodrug thereof are used in the treatment, prevention or reduction of pain in an individual in need thereof, more specifically with acute or chronic pain. Acute and chronic pain is intended to include, but is not limited to, at least one of the following: neuropathic pain, nociceptive pain, psychogenic or somatogenic pain, diabetic neuropathic pain, post-herpetic pain, low-back pain, radiculopathy pain, musculoskeletal pain, post-operative and post-traumatic pain, phantom pain, surgical pain, wound associated pain, chemotherapy-induced peripheral neuropathic pain, short-term/acute or long-term/chronic inflammatory pain, rheumatic pain, arthritic pain, pain associated with osteoarthritis, myofascial pain, migraine, orofacial chronic pain, trigeminal neuralgia, pain associated with cancer, pain associated with fibromyalgia, hyperalgesia syndromes, pain associated with infections, HIV related pain, sprains and strains, hyperalgesia, somatogenic pain, psychogenic pain, heat induced pain, physical pain, nociceptive pain, rheumatic pain, headache, pelvic pain, bladder pain, myofascial, vascular pain, migraine wound, wound associated pain, arthritic pain, somatic visceral pain, phantom pain, radiculopathy, lumbar pain, visceral pain, bowel pain, and pain associated with osteoarthritis.

Embodiment 15. The compounds of formula I, II, III and IV, pharmaceutical salts or prodrug thereof are used in the treatment of autoimmune disorders, due to effects described upon Kv1.3, a target for such disorders.

Embodiment 16. The compounds of formula I, II, III and IV, pharmaceutical salts or prodrug thereof are used in the treatment of diabetes, considering their effect on Kv1.3 channel believed to be related to insulin-sensitivity, insulin-resistance related syndromes and obesity.

Embodiment 17. The compounds of formula I, II, III and IV, pharmaceutical salts or prodrug thereof are used as antiepileptic and antiseizures agents.

Embodiment 18. The compounds of formula I, II, III and IV, for use in the treatment or prophylaxis of a disease in which Kv1.3 channels are involved.

Embodiment 19. A pharmaceutical composition comprises a pharmacologically acceptable diluent or carrier and a combination of active ingredients, wherein said active ingredients comprise at least one compound according to formula I, II, III and IV or a pharmacologically acceptable salt or prodrug thereof.

Embodiment 20. A method of treating pain in a subject in need thereof, comprising administering to the subject having pain a therapeutically effective amount of a compound of formula I, II, III and IV.

Embodiment 21. The method according to embodiment 19, wherein the pain is of an acute and chronic pain types selected from neuropathic pain, nociceptive pain, psychogenic or somatogenic pain, diabetic neuropathic pain, post-herpetic pain, low-back pain, radiculopathy pain, musculoskeletal pain, post-operative and post-traumatic pain, phantom pain, surgical pain, wound associated pain, chemotherapy-induced peripheral neuropathic pain, short-term/acute or long-term/chronic inflammatory pain, rheumatic pain, arthritic pain, pain associated with osteoarthritis, myofascial pain, migraine, orofacial chronic pain, trigeminal neuralgia, pain associated with cancer, pain associated with fibromyalgia, hyperalgesia syndromes, pain associated with infections, HIV related pain, sprains and strains, hyperalgesia, somatogenic pain, psychogenic pain, heat induced pain, physical pain, nociceptive pain, rheumatic pain, headache, pelvic pain, bladder pain, myofascial, vascular pain, migraine wound, wound associated pain, arthritic pain, somatic visceral pain, phantom pain, radiculopathy, lumbar pain, visceral pain, bowel pain, and pain associated with osteoarthritis.

Embodiment 22. A method of treatment or prophylaxis of a disease in which Kv1.3 channels are involved in a subject in need thereof, comprising administering a therapeutically effective amount of a compound of formula I, II, III and IV to a subject in need of treatment or prophylaxis of a disease in which Kv1.3 channels are involved.

Embodiment 23. A method of treatment of an autoimmune disease in a subject in need thereof, comprising administering a therapeutically effective amount of a compound of formula I, II, III and IV to a subject having an autoimmune disease.

Embodiment 24. A method of treatment of diabetes or insulin resistance syndromes in a subject in need thereof, comprising administering a therapeutically effective amount of a compound to a subject having diabetes or an insulin resistance syndrome.

Embodiment 25. A method of treatment of epilepsy or seizures in a subject in need thereof, comprising administering a therapeutically effective amount of a compound to a subject having epilepsy or seizures.

Embodiment 26. The method according to embodiments 20 through 23, wherein the compound is administered in a therapeutically effective amount between 0.018 and 1.8 mg/kg.

Embodiment 27. The compound, composition, use, or method disclosed here, wherein the compound is a compound of formula I, wherein
X is O;
Y is CH;
Z is C;
R$^1$ is alkyl;
R$^2$ is —CH$_2$—R$^3$; wherein R$^3$ is —R$^4$-R$^5$; wherein R$^4$ is alkyl and R$^5$ is heteroaryl;

Q is C;

D is C;

A is —R⁶-R⁷; wherein R⁶ is alkyl and R⁷ is heteroaryl;

E is H; and

J is H.

Embodiment 28. The compounds according to embodiments 1 through 6, wherein the compound is isolated or synthetically produced.

Embodiment 29. The compounds according to embodiments 7 through 28, wherein the compound is nitenin or dihydronitenin.

The present disclosure discloses robust evidence that nitenin and nitenin analogue compounds may be used as analgesics for the treatment, prevention or reduction of chronic and acute pain. This evidence was obtained from several technical approaches, including ex vivo neuronal preparations, animal models of pain, behavioural readouts of pain, in silico approaches, in vitro toxicity tests and, whole-cell voltage-clamp recordings.

The nitenin analogue compounds of the present application were first obtained from the marine sponge *Spongia agaracina* captured in Sagres, Portugal, but have also been chemically synthesized. As shown in the EXAMPLES, the nitenin-containing extract showed a modulatory effect on potassium currents recorded from rat sdDRGNs (pain-sensing neurons), a bioactivity that was the base of a bio-guided fractionation process. The series of obtained fractions allowed the identification of compounds that not only kept the capacity of modulating the $K^+$ currents, but also showed high levels of potency. Results were also confirmed in small diameter trigeminal ganglion neurons (sdTGNs) that showed identical pharmacological effects in very similar $K^+$ current profiles.

The $K^+$ currents affected by the identified compounds, recorded from sdDRGNs (and sdTGNs) by whole-cell voltage-clamp techniques, were object of intensive research by the applicant in the area of pain neurophysiology. The use of rat pain models was fundamental to perform previous target validation, i.e., to determine the $K^+$ current component differentially expressed in pain conditions. In one aspect of the disclosure, it is suggested that the $K^+$ current component affected with pain condition is the one principally modulated (diminished) by the compound(s) of interest. The nature of the recorded modulatory effect on the currents was studied by monitoring several biophysical parameters, such as voltage dependencies of activation and inactivation and kinetics. The specificity of the bioactivity was carried out by comparing the pharmacological effect on currents recorded from the sdDRGNs with those in other types of dorsal root ganglia (medium and large diameter DGRs).

Additionally, drug sensitivity to different voltage-activated channels was assessed by studying the drug effect on currents recorded from chinese hamster ovary (CHO) cells stably transfected with different human Kv channel subunits (Kv1.1, Kv1.2, Kv1.3, Kv1.4 and Kv1.6). The compound is mostly active on hKv1.3 ($IC_{50}$~190 nM), which is 6 to 30 times more sensitive than the other Kv1.xs tested.

One of the competitive advantages of nitenin and nitenin analogue compounds over other compounds used in pain therapy, including those acting on ion channels, lies, in part, in at least eight of its properties which, although inter-related can be described as follows:

1—Nitenin and nitenin analogue compounds are small molecules that are synthesizable using chemistry synthesis approaches;

2—Their novel mode of action and the location and nature of their cellular target: nitenin reduces the activity of $K_V$ channels expressed in snDRGs (a subset of Kv1.x with higher affinity to Kv1.3), responsible for the slow delayed rectifying current, which modulate pain signalling and propagation towards the brain. Together with this peripheral effect of nitenin and nitenin analogues, a complementary central effect is not to be ruled out. Currently, there is a significant and unmet need for specific blockers of some of such Kv1.x channels (e.g. Kv1.3 and Kv1.6) with clinical potential.

3—Administering nitenin or nitenin analogue compounds does not result in any loss of sensorial and nociceptive capacities and nociception of the uninjured limbs/body parts, a feature that relates to its mode of action, for example, to the fact that it is an open channel-dependent effect.

4—The nitenin and nitenin analogue compounds of the present disclosure are easily administrated. In the animal models used to test the nitenin analogue compounds, intravenous (IV) and intraperitoneal injections were used with success regarding its analgesic effect. Importantly, the nitenin analogue compounds can be also administered orally, thus in a preferable embodiment, given the fact that endogastric administration was also performed in the animal models with similar analgesic effects.

5—Based on the toxicological experiments performed, there are no signs of any toxicity or side effects on the systems tested and described below. Given that nitenin acts mainly in the peripheral nervous system (but not exclusively), brain-derived toxicity/side effects have not been shown to occur.

6—Nitenin and its analogues are effective on mitigating pain in a number of pain models, including acute and neuropathic chronic pain, chemotherapy-induced peripheral neuropathy, acute and long-term or chronic inflammatory pain (nociceptive pain), orofacial chronic pain and diabetic neuropathic chronic pain. Such results anticipate a wide range of possible clinical applications.

7—Although also effective in acute/short-term pain, nitenin is particularly effective on long-term/chronic forms of pain; and 8—By acting specifically in a subset of potassium channels (Kv1.x), and not having any effect on sodium currents/channels ($Na_v$s), the nitenin analogue compounds will not compete with Nav modulatory agents but rather, they may eventually be applied in combination with those, maximising the envisaged analgesic effect or acting in a synergistically manner.

In one embodiment, the compounds of the disclosure, or pharmaceutically acceptable salts and prodrugs thereof may be used to treat acute pain. Examples of situations of acute pain, a type of pain that typically lasts less than 3 to 6 months, include surgery, broken bones, dental work, burns and cuts, pain that is directly related to soft tissue damage such as a sprained ankle, labor and childbirth In one embodiment, the compounds of the disclosure, or pharmaceutically acceptable salts and prodrugs thereof may be used to treat chronic pain. Examples of diseases or disorders associated with chronic pain include peripheral neuropathy chronic pain Arthritis, especially osteoarthritis, Cancer, HIV, Diabetes, Fibromyalgia, Shingles, Herpes, Headache, Migraines, Multiple sclerosis, Nerve damage (neuropathy), Low back pain, Trauma and other injuries (eg, herniated disk, torn ligament), Sciatica, Diabetic neuropathy, Carpal tunnel syndrome, Trigeminal neuralgia, post-surgical, Chronic Fatigue Syndrome (or Myalgic Encephalomyelitis), Endometriosis, Inflammatory Bowel Disease, irritable bowel Syndrome, Crohn's disease, Ulcerative colitis, Interstitial Cystitis, Temporomandibular Joint Dysfunction (TMJ), Vulvodynia, Bursitis, Celiac disease, Lupus, Rheumatoid Arthritis, Complex Regional Pain Syndrome, Myofascial pain syndrome, Meningitis, Lyme and other tick-borne diseases, Muscle strains and Sprains.

In some embodiments, the compounds of the disclosure, or pharmaceutically acceptable salts and prodrugs thereof, can be used to treat hyperalgesia, somatogenic pain, psychogenic pain, heat induced pain, physical pain, nociceptive pain, rheumatic, headache, pelvic pain, bladder pain, myofascial, vascular pain, migraine wound, wound associated, arthritic, somatic visceral, phantom pain, radiculopathy, lumbar pain, or pain associated with osteoarthritis.

Both acute and chronic pain involves the complex alteration of the processing and conduction of electrical signals from peripheral nerves to the central nervous system (CNS). The electrical excitability and activity levels of a normal condition, or those related to chronic pain, are result of the inflow or outflow of charged metal ions such as sodium ($Na^+$), potassium ($K^+$) or calcium ($Ca^{2+}$) through membrane ion channels (Nav, Kv or Cav, respectively), causing the generation, propagation and transmission of electric signals throughout the cell and from cell to cell. In chronic pain, the neuronal network underlying pain signalling is altered, with abnormal ionic currents brought by altered expression and biophysics of the underlying channels, resulting in excessive and sustained neuronal excitability and activity. Therefore, an effective analgesic would need to be able to suppress the hyperexcitability of the pain signalling network, restoring the physiologic expression and/or biophysical profiles of the functioning channels, and, in turn, restoring the network activity to resting levels.

Small-diameter DRG neurons (c-fibers), also called pain-sensing neurons, are located outside of the spinal cord that carry the nociceptive input to the CNS (i.e, leading to 'pain'). Usually, in normal conditions, these neurons do not have spontaneous firing activity—they are silent (e.g Ly et al., 2018)-, situation that changes during pain episodes and, indeed with chronic pain. The present underlying therapeutics strategy is to target key ion channels localized in such neurons in the DRG neurons and those in trigeminal ganglia (TG), to "switch-off" such 'pain-induced' hyperexcitability. Consequently, the transmission of the "pain signal" to the CNS is interrupted or diminished, preventing, this way, brain perception of pain. It is possible however that, complementary, there is an effect in central neurons, cooperating into the analgesic effect.

In some embodiments, the compounds of the disclosure, or pharmaceutically acceptable salts and prodrugs thereof may be used to halt pain-induced hyperexcitability. In some embodiments, they can be used to modulate the brain's perception of pain.

Several ion channels have been identified as key effectors in pain propagation. Some are particularly present in these pain-sensing neurons. Therefore, specifically modulating their activity would block pain without affecting other body functions. It is disclosed herein that nitenin analogues are specific modulators of slow voltage-activated $K^+$ currents recorded from the small diameter (sdDRGNs also sdTGNs, thought to correspond with c-fibers). Underlying such slow current are certain Kv1.x channels. This effect is lower in large diameter neurons at a sub micromolar concentration range, i.e. at concentrations below 1 micromolar, the modulatory effect of nitenin is exclusive for sdDRGNs and sdTGNs.

In some embodiments, the compounds of the disclosure, or pharmaceutically acceptable salts and prodrugs thereof may be used to modulate slow-voltage activated $K^+$ currents.

In some embodiments, the currents are from the small diameter (sdDRGNs also sdTGNs) neurons.

Kv1.x, including those mediating slow voltage-activated currents, are ion channels involved in pain signal propagation as principally present in pain-sensing neurons. The nitenin analogue compounds are particularly effective on the slow $K^+$ current-component, sub current-component that, considering the kinetics and voltage dependence of the nitenin-sensitive current, strongly suggests the involvement of a subset of Kv1.x channels. In fact, voltage-clamp tests on currents, recorded from CHO cells stably transfected and expressing hKv1.1, hKv1.2, hKv1.3, hKv1.4 or hKv1.6, showed that the nitenin analogue compounds are much more effective on the Kv1.3 channel (around 6-fold more sensitive to nitenin when compared to the second most sensitive channel (Kv1.2), and around 30-fold more sensitive when compared to the one with the lowest sensitivity) (Kv1.4) (see FIG. 2).

In some embodiments, the compounds of the disclosure, or pharmaceutically acceptable salts and prodrugs thereof may be used to stop hyperexcitability in central neurons, namely neurons under episodes of seizures. The mentioned effect on Kv1.x channels resulting in abolishing repetitive neural firing is the basis for an anti-epileptic effect. Hence the nitenin and nitenin analogues may be used as antiepileptic and antiseizures agents.

In some embodiments, the compounds of the disclosure, or pharmaceutically acceptable salts and prodrugs thereof may be used as blockers of Kv1.3. Kv1.3 has been described as a target for treatment of immunological related pathologies as well as a target for treatment of diabetes and other metabolic disorders. The compounds of the disclosure may be used in the treatment of diabetes and other metabolic disorders.

In some embodiments, the compounds of the disclosure, or pharmaceutically acceptable salts and prodrugs thereof may be used to treat autoimmune diseases. In other embodiments, they may be used to increase insulin sensitivity.

With regard to these therapeutic treatments, the mode (or modes) of administration, dosage (or dosages), and optimized pharmaceutical form (or forms) can be determined according to criteria generally considered during the establishment of a treatment of a patient, such as, by way of non-limiting examples, the potency of the compound(s) and/or pharmaceutically acceptable salts of the compound (s), the age of the patient, the body weight of the patient, the severity of the patient's condition (or conditions), the patient's tolerance to the treatment, and secondary effects observed in treatment. Determination of dosages effective to provide therapeutic benefit for specific modes and frequency of administration is within the capabilities of those skilled in the art.

EXAMPLES

In Vivo and Ex Vivo Pain Models

The rat pain models used for both in vivo behaviour work and for the electrophysiological ex vivo studies were:
   Naïve Wistar: control rats; neurons from the dorsal root ganglia (DRG), lumbar 4, 5 and 6 (L4, L5 and L6).
   Acute and chronic neuropathic pain rat model: CCI rats (chronic constriction of the sciatic nerve of Wistar rats) 3 days (for acute) and 23 to 29 days (for chronic) after surgery; neurons from DRGs (L4, L5 and L6).
   Acute and long-lasting or chronic inflammatory pain rat model: CFA rats (knee administrations of Complete Freund's Adjuvant (CFA) on Wistar rats) with 3 days (acute), 18 days (sub-chronic) and 23 days (chronic) after injection; neurons from DRGs (L3, L4 e L5).

Chronic orofacial pain (COP) rat model: COP rats, with CFA injection in the whisker pad of Wistar rats, analysed 28-30 days after injection; neurons from trigeminal ganglia.

Diabetic Neuropathic pain rat model: STZ rats, Wistar rats were submitted to intraperitoneal injections of STZ (streptozotocin), developed signs of pain 30 days after, and at the end of further 30 days, were tested with nitenin (IV) (60 days total); neurons from DRGs (L4, L5 e L6).

Chemotherapy-induced peripheral neuropathy chronic pain rat model: CIPN rats, Wistar rats submitted to 3 sessions (intra-peritoneal injections) of paclitaxel (every 2 days), tested 42 days after induction; neurons from DRGs (L4, L5 e L6).

For the electrophysiological recordings of the ex vivo material, voltage-clamp recordings were performed on neurons isolated from rat DRGs (and TGs). Recordings were performed from the soma that often contained the proximal fraction of axon, 1 hour after the end of the cell isolation process (includes enzymatic and mechanical treatment).

Mode of Action:

The mode of action of nitenin (represented herein as the compound of formula V) and nitenin analogue compounds (exemplified herein as the compounds of formula I-IV and VI-VIII) as analgesic is disclosed herein for the first time. It involves reduction of $K^+$ currents rather than their potentiation. For such reason, it is important to characterise first the potassium currents present in the sdDRGNs and in sdTGNs.

The voltage activated whole-cell $K^+$ currents recorded from sdDRGNs upon a depolarizing step (say, to +40 mV lasting a second, as in FIG. 1) showed a fast activation followed by two phases of inactivation. The current decay at depolarised potentials are thus better fit by a sum of two exponential functions: a relatively fast component (here termed $I_{fast}$—associated to what is known as A-current), showing a time course ($\tau_{fast}$) of tens of milliseconds, followed by a much slower inactivating current(here termed $I_{slow}$), showing a time course ($\tau_{slow}$) of hundreds of milliseconds (see FIG. 1). Different proportion for $I_{fast}$ and $I_{slow}$ are found from cell to cell and even some cells show only one component, $I_{slow}$. The currents found in sdDRGns are very similar to those described for sdTGns.

Nitenin inhibited the $K^+$ currents from sdDRGNs and from sdTGNs in a dose dependent manner. In concentrations up to 1 μM (~0.3 μg/ml), it specifically reduces $I_{slow}$ (see FIG. 1.b), current component of which becomes over expressed (in relation to $I_{slow}$), in sdDRGn neurons (and in sdTGns) obtained from 'injured nerves' from chronic pain rat models (CCI, CFA and Orofacial). In the typical example presented in FIG. 1.b, one can note that the peak current is mostly unaltered by nitenin treatment whereas the slower component is indeed reduced. The nitenin sensitive current-component (trace subtraction at the bottom of the Figure) shows a current decay that is better fit by a single exponential of ~150 ms, further suggesting that, at moderate concentrations, nitenin effect is specific on $I_{slow}$. In contrast, $I_{fast}$, was little affected by nitenin at concentrations up to 1 μg/ml; concentrations above 3 μM/ml were needed to reduce $I_{fast}$. Importantly, nitenin reductions of $I_{slow}$ were larger in neurons obtained from chronic pain animals when compared from the reductions evoked by some concentrations of nitenin in neurons obtained from 'control' animals.

Nitenin effect is specific to $K^+$ currents, not being able to induce relevant changes on voltage-activated $Na^+$ currents (FIG. 1.b)

The differential dose responses on $I_{slow}$ and $I_{fast}$ are better discerned in the dose-response curves presented in FIG. 2.a. The concentration/blockage relationship for $I_{slow}$ shows a dual phase. Up to one to 1 μM (~0.3 μg/ml), the relationship can be fit by a single Hill function with a $I_{slow}$ of ~0.12 μM. For larger concentrations, the relationship for $I_{slow}$ follows a second phase where the effect on the $I_{slow}$ is added to the effect on $I_{fast}$. Indeed, this second phase coincides with the concentration/blockage relationship for $I_{fast}$, that in turn, is better fit by a single Hill function. Its $IC_{50}$ of ~6 μM confirms a much lower sensitivity to Nitenin.

The higher sensitivity of nitenin to $I_{slow}$ (rather than $I_{fast}$) and the nature of the nitenin sensitive current (see nitenin sensitive current in FIG. 1.b) urged to understand which $K^+$ channel(s) do underline $I_{slow}$. By considering which Kv channel subunits are known to be expressed in DRG, and the biophysical nature of the nitenin-sensitive current, nitenin was tested on whole-cell currents recorded from CHO cells expressing hKv1.1, hKv1.2, hKv1.3, hKv1.4 and hKv1.6. From such list, only Kv1.4 would underlie the 'A-type' $I_{fast}$ and the remaining, could participate in $I_{slow}$. Results are summarised in FIG. 2.B showing dose response with the relative sensitivity to nitenin. Current inhibition was measured at the end of the 1000 ms pulse. Kv1.3 showed the higher sensitivity with an $IC_{50}$ of 190 nM, an actual value in the same range of the dose response for $I_{slow}$ from sdDRGNs (IC50 $I_{slow}$~120 nM). In contrast, hKv1.1, hKv1.2 and hKv1.6 showed a ~6× lower (or less) sensitivity and, hKv1.4, ~30× less sensitive, clearly the least sensitive.

Nitenin inhibition of slow $K^+$ currents involves a pharmacological process of 'open-channel blockage'. Also, it involves a change in the voltage dependence of steady state of inactivation (and little or no change for the voltage dependence of activation). In fact, nitenin shifts to more hyperpolarised potentials the I-V curves related to the voltage dependence of inactivation (see FIG. 3).

The compounds inhibit slow voltage-activated currents recorded from sdDRGNs by promoting $K^+$ channel inactivation, inactivation of which, is somewhat impaired in chronic pain conditions. More precisely, the compounds shift the voltage sensitivity of the steady-state inactivation to less depolarised values (or more hyperpolarised), facilitating inactivation. Such compound-evoked shift in inactivation is as greater as more depolarised the voltage curve profile is in the first place (before treatment with nitenin or nitenin analogues). Depolarised Inactivation curves are typical from sdDRGNs obtained from chronic pain conditions. In other words, in neurons obtained from injured nerves (chronic), nitenin reverts the voltage dependence profile of inactivation to 'control' patterns. Consequently, the compound-evoked shift in the voltage sensitivity of inactivation is higher in neurons from injured nerves (that exhibit an abnormally depolarized profile) and lower in unaffected neurons that show hyperpolarised voltage profiles. This interesting effect on channel gating explains in part the compound-evoked decrease of neuronal excitability that is specific/more pronounced in affected neurons, i.e. during pain.

C-fibers are usually silent, with little or no spontaneous firing activity, i.e., there is little or no basal activity in control conditions. We start by analysing the nitenin effect on the un-injured silent neurons. Given the nature of nitenin mode of action, one would expect little or no effect of nitenin on $K^+$ currents in such 'silent neurons', because, being an open-channel blocker, the effect is activity-dependent (also, the nitenin shift in inactivation curves should be minimal). Nevertheless, in this case of unaffected neurons, there is moderate decrease of K$^+$ currents, but such effect would not reach a threshold potential for inducing repetitive firing (due to insufficient evoked depolarization). This explains in part why nitenin does not change the "pain perception" in non-affected body regions. On the other hand, in the occurrence of chronic pain, there is an hyperexcitable state in the injured neurons, with repetitive and sustained firing. In this hyperexcitable neurons, the nitenin effect is maximal (as explained above). A further increase of the resting potential (induced by the nitenin-induced reduction of K$^+$ currents) will dictate a firing failure brought by indirect promotion of inactivation of sodium channels. The signal is therefore interrupted but only on the 'injured' fibers.

Lastly, regarding specificity, it is important to note that the slow currents obtained from large diameter DRG neurons are around 10 times less sensitive to nitenin.

How the nitenin effect on Kv currents results in the analgesic effect consists in a new mode of action because, in a conventional way to address this matter, one would expect that an increase of K$_V$ currents, rather than an inhibition, would calm down neuroexcitability of the hyperexcitable C fibers. In the present case, one must stress that slowly inactivating-potassium currents ($I_{slow}$) are functionally more expressed in comparison with the fast inactivating currents ($I_{fast}$), in chronic pain conditions (sdDRGns obtained from CCI, CFA and STZ, and, sdTGns from COP rat model). Also important to note is that, in such conditions, $I_{slow}$ shows abnormal depolarised inactivation profiles, i.e. channels inactivating less. In order to sustain repetitive firing for long periods, the typical situation under chronic pain, the increase of the "excitatory force" brought by the consensual increase in Na$^+$ currents, has to be sustained by a counter-balancing increase in K$^+$ currents that would accommodate repetitive-long-term firing patterns. The effect of the compounds disclosed herein is such that it reverts such patterns to control profiles, decreasing the slowly-inactivating Kv-mediated current. This nitenin-evoked effect of the slow K$^+$ currents would not allow the required accommodation of the increase of sodium conductance (Nav), typical in pain situations. As a result, the exacerbated sodium currents would inactivate in the presence of nitenin (also due to a depolarization evoked by the decrease of Kv currents), switching off spike firing in the affected nerves but not in normal, uninjured neurons. This means that, during pain, namely, in chronic pain, Kv blockers, and not only the Kv potentiators or openers, should be considered as potential analgesics.

How a reduction of K$^+$ currents result in a marked decrease of neuronal excitability can be explained in different ways or, most likely, by a combination of phenomena.

Firstly, as mentioned above, the drug-induced decrease of K$^+$ currents may result in a slow depolarization of the affected neurons in a way that membrane potential is kept at a depolarized level, so the usual threshold potential may pass without an action potential having been fired. It would thus result in an accommodation-like process as depolarization would close inactivation gates of the Na$^+$ channels, remaining closed, preventing the upstroke of action potential to occur (not enough Na$^+$ channels 'activatable').

Secondly, one may consider a more direct role of the specific blockage on Kv1.3, as (1) nitenin is particularly effective on Kv1.3 (see FIG. 2.b) and (2) Kv1.3 expressed in DRG (Yang et al., 2004) and increases it expression levels in DRG neurons with chronic pain (unpublished data). The biophysical nature and the kinetics of Kv1.3 mediated currents are thought to sustain stabilised tonic firing (Kupper et al., 2002), a state that correspond to neurons in a 'chronic pain situation'. Reducing such Kv1.3 mediated currents would lead to a decrease in action potential amplitudes and into a stationary depolarised state with no firing, as found in rat hippocampal neurons (Kupper et al., 2002).

Efficacy Results:

For efficacy studies, nociception was assessed in all animals from all pain models by regular behavioural monitoring, by quantifying the sensitivity to mechanical stimuli with Von Frey filaments, and consequently reflecting hyperalgesia when hypersensitive. For the Neuropathic pain model CCI, the cold allodynia with acetone test was also used and showed very similar responses as those with Von Frey Filaments.

Efficacy after intravenous administration. The following results concern intravenous (IV) injections of purified nitenin (>98%—compound of formula V) (1 μg/mL of blood ~0.06 mg/Kg.

Naïve Wistar controls: There was never any change in sensitivity scores following I.V. injections of nitenin, for both paws.

With CCI rats, following I.V. administrations, there was a noticeable decrease of sensitivity to mechanical stimuli for both acute (3 days after induction of the model) and chronic (22 or 31 days) situations. Atypical experiment is presented in FIG. 4. The nitenin-induced decrease of hypersensitivity was robust in both cases (acute and chronic) but clearly higher in the case of chronic pain; in some individuals nitenin reverted the scores to control values. The duration of the pain mitigation lasted for 2 to 4 hours. Importantly, there were no changes in the behavioural scores of the contralateral (uninjured) paw for all the animals tested.

With CFA rats, there was a noticeable decrease of sensitivity to mechanical stimuli after nitenin I.V. injection for all situations: 3 days (acute), 18 days (sub-chronic, intravenous) and 23 days (chronic). Again, the nitenin effect was higher in the situation of chronicity even if, with 23 days, there was already a partial recovery of the scores. The duration of the pain mitigation lasted for 2.5 to 4.5 hours and, as with the CCI rats, was confined to the injured paw.

With COP rats, nitenin I.V. administration consistently resulted in a marked reduction of mechanical sensitivity, assessed at the whisker pad region 23 days after the injection of CFA (chronic). A typical experiment is presented in FIG. 5. The duration of the pain mitigation lasted for 3 to 4 hours and was confined to the injured whisker pad (injured face-side only).

For STZ rats, animals have reached diabetic glucose blood levels within a week of STZ injection and hypersensitivity to mechanical stimuli, at the end of 30 days. Therefore, nitenin was only I.V. administered, 60 days after treatment with STZ, allowing time for chronic diabetic neuropathy establishment. Following nitenin administration, we observed a decrease of mechanical sensitivity in the hypersensitive paws. The duration of the nitenin-induced pain mitigation lasted for 2 to 3 hours.

With CIPN rats, nitenin was administered I.V. 42 days after treatment with paclitaxel, consistently resulting in an intense decrease of sensitivity to mechanical stimuli, in both paws. Nevertheless, the mitigation of pain, in this case, was less strong and not as long-lasting (<2 hours), when compared with the other pain models, probably due to the severity of the model.

Efficacy after intraperitoneal administration. Intraperitoneal administration was tested in CFA rats (23 days after CFA injection), with 10 times the nitenin quantity administered by I.V. injections. In this case, there was a clear mitigation effect of pain with score values reaching control levels, effect that lasted for about 4 hours.

Efficacy after oral administration. Oral administration of nitenin through stomach gavages (endogastric), with 100 times the quantity administered by I.V. injections, was tested in CCI rats (31 days after surgery). In all animals tested, there was similar mitigation of pain, i.e., a decrease in the sensitivity values. Such effects lasted for about 2 hours.

In addition to the tests performed with nitenin, 3 analogues (compounds of formula VI, VII and VIII) designed around the core structure of formulas I, II, III and IV were also tested to demonstrate activity.

In summary, nitenin compounds have shown to be effective for short-term/acute and long-term/chronic neuropathic pain, short-term/acute and long-term/chronic inflammatory pain, chronic orofacial pain, diabetic neuropathic pain, and chemotherapy-induced peripheral neuropathy. Efficacy has been demonstrated for several administration routes, such as intravenously, intraperitoneally and, importantly, via oral administration.

The effects of the three nitenin analogues were similar in what the affected K$^+$ current component is concerned. However, the typical effects on $I_{slow}$ (FIG. 7-9), and on the voltage dependence of steady-state inactivation (FIGS. 10-12) were obtained at different concentrations. This strongly indicates that nitenin analogue compounds have a clear effect on $I_{slow}$, although with different affinities. The strongest effect was observed for the compound of formula V, followed by the compounds of formula VII, VIIIa, VIIIb and VI, respectively.

Based in dose dependent curves, where several concentrations where applied I.V. and efficacy levels were consequently quantified, Nitenin analogs should be used for pharmacological use in warm-blooded vertebrates, particularly humans, in doses ranging from 0.1 μg/ml blood (6 μg/Kg body weight) to 30 μg/ml blood (1.8 mg/Kg body weight).

Toxicity Results:

The toxicity of nitenin compounds were assessed by different techniques. No signs of toxicity were detected.

1. Assays of In Silico Toxicity

Assays with the VEGA® software allowed to test several types of toxicity: mutagenicity, carcinogenicity, developmental toxicity, hepatotoxicity, dermal sensitisation, affinity to oestrogen receptor and several environmental parameters (e.g. aquatic toxicity, bees, bioaccumulations). At various levels of confidence, all tests were negative.

2. In Vitro and Ex Vivo Toxicity

Cell viability tests (MTS) using cell lines HFF2 did not show any reduction in cell viability for concentrations up to 200 μM.

Cardiotoxicity:

a) Cell viability tests (MTS) using mouse cardiomyocytes primary cultures did not show any reduction in cell viability for concentrations up to 20 μM.

b) Whole-cell voltage-clamp in hERG: No effect on the outward currents mediated by hERG expressed in HEK (human embryonic kidney) cells.

c) Ex vivo rat preparations revealed that nitenin (up to 10 μM) does not change sinus heart rate, atrial inotropy (in isolated rat atria) and right ventricular (RV) inotropy (in isolated rat ventricles).

d) In vivo electrocardiogram (ECG) recordings of anesthetized Wistar rats revealed that nitenin intravenous injections (60 μg/Kg) did not change sinus rhythm and heart rate neither induced arrhythmia or any pro-arrhythmic phenomena.

3. In Vivo Toxicity

For all in vivo administrations, the behaviour of the animals was followed for an additional week, period after which post mortem necropsies were conducted. A set of individuals were subjected to two I.V. administration per day (one in the morning and one other at the end of the afternoon) for an entire week. No alterations of any aspect on any organ or internal structure were detected.

Several features are described hereafter that can each be used independently of one another or with any combination of the other features. However, any individual feature might not address any of the problems discussed above or might only address one of the problems discussed above. Some of the problems discussed above might not be fully addressed by any of the features described herein. Although headings are provided, information related to a particular heading, but not found in the section having that heading, may also be found elsewhere in the specification.

In the foregoing specification, embodiments of the invention have been described with reference to numerous specific details that may vary from implementation to implementation. Thus, the sole and exclusive indicator of what is the invention, and is intended by the applicants to be the invention, is the set of claims that issue from this application, in the specific form in which such claims issue, including any subsequent correction. Any definitions expressly set forth herein for terms contained in such claims shall govern the meaning of such terms as used in the claims. Hence, no limitation, element, property, feature, advantage or attribute that is not expressly recited in a claim should limit the scope of such claim in any way. The specification and drawings are, accordingly, to be regarded in an illustrative rather than a restrictive sense.

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

BIBLIOGRAPHIC REFERENCES

Li Y, North R Y, Rhines L D, Tatsui C E, Rao G, Edwards D D, Cassidy R M, Harrison D S, Johansson C A, Zhang H, Dougherty P M. (2018). DRG Voltage-Gated Sodium Channel 1.7 Is Upregulated in Paclitaxel-Induced Neuropathy in Rats and in Humans with Neuropathic Pain. J Neurosci. 2018 Jan. 31; 38(5):1124-1136.

Kupper J, Prinz A A, Fromherz P (2002). Recombinant Kv1.3 potassium channels stabilize tonic firing of cultured rat hippocampal neurons. Pflugers Arch. February; 443(4): 541-7.

Yang E K, Takimoto K, Hayashi Y, de Groat W C, Yoshimura N. (2004). Altered expression of potassium channel subunit mRNA and alpha-dendrotoxin sensitivity of potassium currents in rat dorsal root ganglion neurons after axotomy. Neuroscience; 123(4):867-74.

What is claimed is:

1. A compound of formula I, II, or III, or a pharmaceutically acceptable salt thereof,

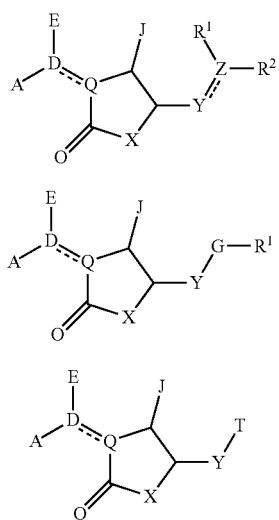

wherein
— represents a carbon-carbon single bond or a carbon-carbon double bond;
X is selected from O, NH, CH$_2$;
Y is selected from CH, CH$_2$;
Z is selected from C, N;
G is selected from O;
T is selected from, SH;
One of R$^1$ and R$^2$ is H, and then R$^1$ is selected from alkenyl, cycloalkyl or —CH$_2$—R$^3$ or R$^2$ is selected from alkyl, alkenyl, cycloalkyl, aryl or —CH$_2$—R$^3$; wherein for R$^1$, R$^3$ is selected from, cycloalkyl, heteroaryl, —R$^4$-R$^5$ and for R$^2$, R$^3$ is selected from aryl, cycloalkyl, heteroaryl, —R$^4$-R$^5$; wherein R$^4$ is selected from alkyl, alkenyl; wherein R$^5$ is selected from aryl, substituted or unsubstituted heteroaryl, substituted or unsubstituted gama-lactone;
Q is selected from C, CH;
D is selected from C, CH;
One of A and E is H and the other is selected from OH, SH, C4 or C7-C12 alkyl, alkenyl, R$^6$-R$^7$, wherein R$^6$ is selected from C2-C12 alkyl, alkenyl, and R$^7$ is selected from substituted or unsubstituted aryl, except phenyl, substituted or unsubstituted heteroaryl, substituted or unsubstituted gama-lactone;
J is selected from H, OH, SH, NH$_2$, and halogen;
wherein the compound is not nitenin, dihydronitenin nor their respective, enantiomers, and stereoisomers;
wherein aryl refers to a monovalent aromatic hydrocarbon radical comprising 6-20 carbon atoms (C6-C20) that is derived by removing a hydrogen atom from an aromatic ring; alkyl refers to a saturated monovalent hydrocarbon radical comprising one to four carbon atoms (C1-C4) and may be linear, or cyclic; heteroaryl refers to a monovalent aromatic radical comprising 5 to 20 atoms, one or more 5-,6-, or 7-membered rings, and one or more heteroatoms independently chosen from nitrogen, oxygen, phosphorous, and sulfur; cycloalkyl is a cyclic alkyl; and alkenyl refers to a monovalent hydrocarbon radical comprising four to eight carbon atoms (C2-C8) with at least one site of unsaturation.

2. The compounds of formula II according to claim 1, or a pharmaceutically acceptable salt, wherein:
X is O;
Y is CH$_2$;
G is O;
R$^1$ is H;
J is H;
Q is C;
D is C;
E is H;
A is —R$^6$-R$^7$; wherein R$^6$ is alkyl and R$^7$ is heteroaryl.

3. The compounds of formula II according to claim 1, or a pharmaceutically acceptable salt or prodrug thereof, wherein
X is O;
Y is CH$_2$;
G is O;
R$^1$ is H;
J is H;
Q is C;
D is C;
E is —R$^6$-R$^7$; wherein R$^6$ is alkyl and R$^7$ is heteroaryl;
A is H.

4. The compound of formula I, II and III, according to claim 1, or a pharmaceutically acceptable salt thereof, wherein R$^7$ is not furan-3-yl.

5. A pharmaceutical composition comprising one or more compounds of formula I, II or III, or a pharmaceutically acceptable salt thereo, and a pharmacologically acceptable diluent or carrier

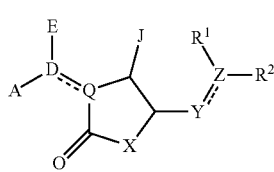

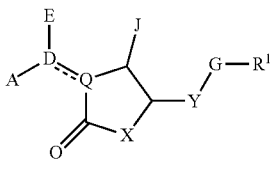

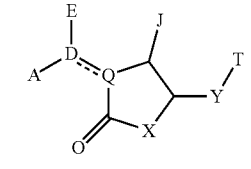

wherein
— represents a carbon-carbon single bond or a carbon-carbon double bond;
X is selected from O, NH, CH$_2$;
Y is selected from CH, CH$_2$;
Z is selected from C, N;
G is selected from O;
T is selected from, SH;
One of R$^1$ and R$^2$ is H, and then R$^1$ is selected from alkenyl, cycloalkyl or —CH$_2$—R$^3$ or R$^2$ is selected from alkyl, alkenyl, cycloalkyl, aryl or $-CH_2-R^3$; wherein for $R^1$, $R^3$ is selected from, cycloalkyl, heteroaryl, $-R^4-R^5$ and for $R^2$, $R^3$ is selected from aryl, cycloalkyl, heteroaryl, $-R^4-R^5$; wherein $R^4$ is selected from alkyl, alkenyl; wherein $R^5$ is selected from aryl, substituted or unsubstituted heteroaryl, substituted or unsubstituted gama-lactone;

Q is selected from C, CH;

D is selected from C, CH;

One of A and E is H and the other is selected from OH, SH, C4 or C7—C12 alkyl, alkenyl, $R^6-R^7$, wherein $R^6$ is selected from C2-C12 alkyl, alkenyl, and $R^7$ is selected from substituted or unsubstituted aryl, except phenyl, substituted or unsubstituted heteroaryl, substituted or unsubstituted gamma-lactone;

J is selected from H, OH, SH, $NH_2$, and halogen;

wherein aryl refers to a monovalent aromatic hydrocarbon radical comprising 6-20 carbon atoms (C6-C20) that is derived by removing a hydrogen atom from an aromatic ring; alkyl refers to a saturated monovalent hydrocarbon radical comprising one to four carbon atoms (C1-C4) and may be linear, or cyclic; heteroaryl refers to a monovalent aromatic radical comprising 5 to 20 atoms, one or more 5-, 6-, or 7-membered rings, and one or more heteroatoms independently chosen from nitrogen, oxygen, phosphorous, and sulfur; cycloalkyl is a cyclic alkyl; and alkenyl refers to a monovalent hydrocarbon radical comprising four to eight carbon atoms (C4-C8) with at least one site of unsaturation.

6. The pharmaceutical composition according to claim 5, wherein:

X is O;
Y is CH;
Z is C;
R1 is alkyl;
R2 is $-CH_2-R^3$; wherein $R^3$ is $-R^4-R^5$; wherein $R^4$ is alkyl and R5 is heteroaryl;
Q is C;
D is C;
A is $-R^6-R^7$; wherein $R^6$ is C2-C12 alkyl and $R^7$ is heteroaryl;
E is H; and
J is H.

7. A pharmaceutical composition comprising a pharmacologically acceptable diluent or carrier and one or more compounds according to anyone of claims 1, 2, 3, and 4, or a pharmacologically acceptable salt thereof.

8. A method of treating or reducing pain in a subject in need thereof, comprising administering to the subject having pain a therapeutically effective amount of a pharmaceutical composition according to claim 5.

9. The method according to claim 8, wherein the pain is of an acute or chronic pain type selected from neuropathic pain, nociceptive pain, psychogenic or somatogenic pain, diabetic neuropathic pain, post-herpetic pain, low-back pain, radiculopathy pain, musculoskeletal pain, post-operative and post-traumatic pain, phantom pain, surgical pain, wound associated pain, chemotherapy-induced peripheral neuropathic pain, short-term/acute or long-term/chronic inflammatory pain, rheumatic pain, arthritic pain, pain associated with osteoarthritis, myofascial pain, migraine, orofacial chronic pain, trigeminal neuralgia, pain associated with cancer, pain associated with fibromyalgia, hyperalgesia syndromes, pain associated with infections, HIV related pain, sprains and strains, hyperalgesia, somatogenic pain, psychogenic pain, heat induced pain, physical pain, nociceptive pain, rheumatic pain, headache, pelvic pain, bladder pain, myofascial, vascular pain, migraine wound, wound associated pain, arthritic pain, somatic visceral pain, phantom pain, radiculopathy, lumbar pain, visceral pain, bowel pain, and pain associated with osteoarthritis.

10. A method of treatment of diabetes or insulin resistance syndromes, epilepsy or seizures in a subject in need thereof, comprising administering a therapeutically effective amount of a composition according to claim 5, to a subject in need thereof.

11. The method according to anyone of claims 8, 9 and 10, wherein the one or more compounds in the composition are administered in a therapeutically effective amount between 0.018 and 1.8 mg/kg.

12. The method of anyone of claims 8, 9, and 10, wherein the compound is nitenin or dihydronitenin, or an enantiomer, stereoisomer, or salt thereof.

13. The method according to any one of claims 8, 9 and 10, wherein the compound is administered in a dose reaching a blood level ranging from 0.1 μg/ml blood to 30 μg/ml blood.

14. A method of treating or reducing pain in a subject in need thereof, comprising administering to the subject having pain a therapeutically effective amount of a pharmaceutical composition according to claim 6.

15. A method of treatment of diabetes or insulin resistance syndromes, epilepsy or seizures in a subject in need thereof, comprising administering a therapeutically effective amount of a composition according to claim 6, to a subject in need thereof.

* * * * *

UNITED STATES PATENT AND TRADEMARK OFFICE
CERTIFICATE OF CORRECTION

PATENT NO. : 12,336,977 B2
APPLICATION NO. : 17/631135
DATED : June 24, 2025
INVENTOR(S) : Pedro Afonso Dos Santos Baltazar De Lima et al.

It is certified that error appears in the above-identified patent and that said Letters Patent is hereby corrected as shown below:

On the Title Page

In Column 1, Item (72), Inventors:
Line 20 delete "Laurent Alain Claudetrembleau" and insert -- Laurent Alain Claude Trembleau --.

Signed and Sealed this
Sixteenth Day of September, 2025

Coke Morgan Stewart
*Acting Director of the United States Patent and Trademark Office*